(12) United States Patent
VanSumeren et al.

(10) Patent No.: US 8,476,326 B2
(45) Date of Patent: Jul. 2, 2013

(54) FIBRILLATED POLYOLEFIN FOAM

(75) Inventors: Mark W. VanSumeren, Midland, MI (US); Luther Stockton, Midland, MI (US); Sue Machelski, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 11/525,551

(22) Filed: Sep. 22, 2006

(65) Prior Publication Data
US 2008/0076844 A1 Mar. 27, 2008

(51) Int. Cl.
*C08J 9/28* (2006.01)
*C08J 9/30* (2006.01)
*C08G 73/10* (2006.01)
*C08K 5/36* (2006.01)
*C08F 290/06* (2006.01)
*C08K 5/00* (2006.01)

(52) U.S. Cl.
USPC .............................. 521/65; 524/392; 524/81

(58) Field of Classification Search
USPC ................... 521/50, 65; 524/81, 392
See application file for complete search history.

(56) References Cited

U.S. PATENT DOCUMENTS

| | | | |
|---|---|---|---|
| 3,585,104 A | 6/1971 | Kleinert | |
| 3,590,000 A | 6/1971 | Palermiti et al. | |
| 3,645,992 A | 2/1972 | Elston | |
| 3,758,643 A | 9/1973 | Fischer | |
| 3,806,558 A | 4/1974 | Fischer | |
| 4,076,698 A | 2/1978 | Anderson et al. | |
| 4,104,210 A | 8/1978 | Coran et al. | |
| 4,130,535 A | 12/1978 | Coran et al. | |
| 4,250,273 A | 2/1981 | Bohm et al. | |
| 4,271,049 A | 6/1981 | Coran et al. | |
| 4,311,628 A | 1/1982 | Abdou-Sabet et al. | |
| 4,340,684 A | 7/1982 | Bohm et al. | |
| 4,447,560 A | 5/1984 | Piersol | |
| 4,486,552 A | 12/1984 | Niemann | |
| 4,543,286 A * | 9/1985 | Harpell et al. | ............. 428/296.4 |
| 4,594,130 A | 6/1986 | Chang et al. | |

(Continued)

FOREIGN PATENT DOCUMENTS

| | | |
|---|---|---|
| JP | 8143804 | 6/1996 |
| JP | 2004155851 | 6/2004 |

(Continued)

OTHER PUBLICATIONS

Notification of Transmittal of the International Search Report and the Written Opinion of the International Searching Authority, or the Declaration; Dated Apr. 4, 2008, 16 Pages.

(Continued)

*Primary Examiner* — Liam Heincer

(57) ABSTRACT

A method for generating a thermoplastic foam from an aqueous dispersion, the aqueous dispersion comprising a thermoplastic resin, water, and a dispersion stabilizing agent, the method including: adding at least one froth stabilizing surfactant to the aqueous dispersion to form a mixture; adding a fiber to the mixture; and frothing the mixture to create a froth, removing at least a portion of the water in the froth to create a foam, wherein the foam generated has a non-cellular fibrillated morphology. In another aspect, embodiments disclosed herein relate to a foam having a thermoplastic-based, fibrillated, non-cellular structure, wherein the foam has an average density of about 0.02 g/cm$^3$ to about 0.07 g/cm$^3$. In certain embodiments, the foam may be used in an absorbent article.

23 Claims, 5 Drawing Sheets

U.S. PATENT DOCUMENTS

| | | | |
|---|---|---|---|
| 4,599,392 A | 7/1986 | McKinney et al. | |
| 4,762,890 A | 8/1988 | Strait et al. | |
| 4,793,898 A | 12/1988 | Laamanen et al. | |
| 4,927,882 A | 5/1990 | Bayan | |
| 4,927,888 A | 5/1990 | Strait et al. | |
| 4,950,541 A | 8/1990 | Tabor et al. | |
| 4,988,781 A | 1/1991 | McKinney et al. | |
| 5,051,478 A | 9/1991 | Puydak et al. | |
| 5,248,729 A | 9/1993 | Inoue et al. | |
| 5,272,236 A | 12/1993 | Lai et al. | |
| 5,278,272 A | 1/1994 | Lai et al. | |
| 5,504,172 A | 4/1996 | Imuta et al. | |
| 5,595,628 A | 1/1997 | Gordon et al. | |
| 5,612,385 A | 3/1997 | Ceaser | |
| 5,677,383 A | 10/1997 | Chum et al. | |
| 5,756,659 A | 5/1998 | Hughes et al. | |
| 5,844,045 A | 12/1998 | Kolthammer et al. | |
| 5,869,575 A | 2/1999 | Kolthammer et al. | |
| 5,938,437 A | 8/1999 | DeVincenzo | |
| 6,051,681 A | 4/2000 | Dozeman et al. | |
| 6,111,023 A | 8/2000 | Chum et al. | |
| 6,261,679 B1 | 7/2001 | Chen et al. | |
| 6,268,444 B1 | 7/2001 | Klosin et al. | |
| 6,316,549 B1 | 11/2001 | Chum et al. | |
| 6,423,183 B1 | 7/2002 | Goulet et al. | |
| 6,448,341 B1 | 9/2002 | Kolthammer et al. | |
| 6,455,636 B2 | 9/2002 | Sanada | |
| 6,538,070 B1 | 3/2003 | Cardwell et al. | |
| 6,545,088 B1 | 4/2003 | Kolthammer et al. | |
| 6,566,446 B1 | 5/2003 | Parikh et al. | |
| 6,603,054 B2 | 8/2003 | Chen et al. | |
| 6,627,670 B2 * | 9/2003 | Mork et al. | 521/65 |
| 6,824,650 B2 | 11/2004 | Lindsay et al. | |
| 6,825,295 B2 | 11/2004 | Klosin et al. | |
| 6,837,970 B2 | 1/2005 | Ko et al. | |
| 6,863,940 B2 | 3/2005 | Silver et al. | |
| 6,897,276 B2 | 5/2005 | Boussie et al. | |
| 6,906,160 B2 | 6/2005 | Stevens | |
| 6,953,764 B2 | 10/2005 | Frazier et al. | |
| 6,960,635 B2 | 11/2005 | Stevens et al. | |
| 7,102,006 B2 | 9/2006 | Vogel | |
| 7,361,694 B2 | 4/2008 | Strandburg | |
| 2002/0200039 | 10/2003 | Adamian Vahe A. | |
| 2003/0200039 A1 | 10/2003 | Adamian et al. | |
| 2003/0220039 A1* | 11/2003 | Chen et al. | 442/327 |
| 2004/0149412 A1 | 8/2004 | Tammi et al. | |
| 2005/0100754 A1 | 5/2005 | Moncla et al. | |
| 2005/0192365 A1* | 9/2005 | Strandburg et al. | 521/50 |
| 2005/0192402 A1 | 9/2005 | Antal et al. | |
| 2005/0271888 A1 | 12/2005 | Moncla et al. | |
| 2006/0019906 A1 | 1/2006 | Satoh et al. | |
| 2006/0198983 A1 | 9/2006 | Patel | |
| 2006/0199006 A1 | 9/2006 | Poon et al. | |
| 2006/0199744 A1 | 9/2006 | Walton et al. | |
| 2006/0199872 A1 | 9/2006 | Prieto et al. | |
| 2006/0199884 A1 | 9/2006 | Hoenig et al. | |
| 2006/0199887 A1 | 9/2006 | Liang et al. | |
| 2006/0199896 A1 | 9/2006 | Walton et al. | |
| 2006/0199897 A1 | 9/2006 | Karjala et al. | |
| 2006/0199905 A1 | 9/2006 | Hughes et al. | |
| 2006/0199908 A1 | 9/2006 | Cheung et al. | |
| 2006/0199910 A1 | 9/2006 | Walton et al. | |
| 2006/0199911 A1 | 9/2006 | Markovich et al. | |
| 2006/0199912 A1 | 9/2006 | Fuchs et al. | |
| 2006/0199914 A1 | 9/2006 | Harris et al. | |
| 2006/0199931 A1 | 9/2006 | Poon et al. | |
| 2006/0205883 A1 | 9/2006 | Loyen et al. | |
| 2006/0211781 A1 | 9/2006 | Strandburg et al. | |
| 2006/0211819 A1 | 9/2006 | Hoenig et al. | |
| 2007/0010616 A1 | 1/2007 | Kapur et al. | |
| 2007/0078222 A1 | 4/2007 | Chang et al. | |
| 2007/0092704 A1 | 4/2007 | Patel et al. | |
| 2007/0141933 A1 | 6/2007 | Wevers et al. | |
| 2007/0244276 A1 | 10/2007 | Datta | |
| 2008/0200891 A1* | 8/2008 | Kim et al. | 604/369 |

FOREIGN PATENT DOCUMENTS

| | | |
|---|---|---|
| JP | 2005140835 | 6/2005 |
| JP | 2005154562 | 6/2005 |
| JP | 2006152222 | 6/2006 |
| WO | 99/61518 | 12/1999 |
| WO | 0001745 | 1/2000 |
| WO | 0340195 | 5/2003 |
| WO | 2004024740 | 3/2004 |
| WO | 2005/021622 | 3/2005 |
| WO | 2005021622 | 3/2005 |
| WO | 2005021638 | 3/2005 |
| WO | 2005/090427 A2 | 9/2005 |
| WO | 2005090425 | 9/2005 |
| WO | 2005090426 | 9/2005 |
| WO | 2007/011728 | 1/2007 |

OTHER PUBLICATIONS

Examiner's First Report dated Mar. 1, 2010 in corresponding Australian patent application No. 2007299638 (2 pages).
Examiner's Written Opinion dated Apr. 6, 2010 in corresponding Singapore patent application No. 200901845-8 (10 pages).
English Patent Abstract of JP2006152222 from esp@cenet, published Jun. 15, 2006, 1 page.
English Patent Abstract of JP2005154562 from esp@cenet, published Jun. 16, 2005, 1 page.
English Patent Abstract of JP2004155851 from esp@cenet, published Jun. 3, 2004, 1 page.
English Patent Abstract of JP2005140835 from esp@cenet, published Jun. 2, 2005, 1 page.
English Patent Abstract of JP8143804 from esp@cenet, published Jun. 4, 1996, 1 page.
PCT International Search Report issued in PCT Application No. PCT/US2007/015493 dated Dec. 17, 2007 (2 pages).
PCT Written Opinion issued in PCT Application No. PCT/US2007/015493 dated Dec. 17, 2007 (4 pages).
PCT International Preliminary Report of Patentabillity and Written Opinion of the ISR issued in PCT Application No. PCT/US2007/015493 dated Jan. 6, 2009, (5 pages).
Examiner's First Report issued Mar. 1, 2010 in corresponding Australian application 2007299638 (2 pages).
Examiner's Written Opinion issued Apr. 6, 2010 in corresponding Singapore patent application No. 200901845-8 (10 pages).
Translation of Official Action dated Jul. 1, 2010 received from the Patent Office of the Russian Federation in corresponding Russian application No. 2009115193 (3 pages).
Communication pursuant to Article 94(3) EPC dated Apr. 30, 2010, received from the European Patent Office in corresponding European application No. 07 843 016.2.
Notice of Reasons for Rejection dated Nov. 22, 2011 from counterpart Japanese Application No. 2009-529419, 3 pages.
Response to Office Action dated Nov. 16, 2011 from counterpart Korean Application No. 10-2009-7008154, 2 pages.
Amended claims dated Nov. 9, 2011 from counterpart Singaporean application No. 200901845-8, 4 pages.
Office Action dated Aug. 10, 2011 from counterpart Taiwanese application No. 96135708 , 4 pages.
Notice of Preliminary Rejection dated Oct. 18, 2011 from counterpart Japanese Application No. 2009-529419, 5 pages.
Examiners Report dated Nov. 8, 2010 from counterpart Canadian Application No. 2,663,860, 3 pages.
Response to Taiwanese Office Action in counterpart Taiwanese Patent Application No. 096125708, dated Dec. 29, 2011, 4 pages.
Japanese Office Action response and cover letter—English language—dated Feb. 20, 2012 from counterpart Japanese Patent Application No. 2009-529419, 3 pages.
Chinese Office Action dated Feb. 25, 2011 with translation for counterpart Chinese Application No. 200780043385.8, 13 pages.
Korean Office Action dated Jan. 20, 2011 with translation for counterpart Korean Application No. 10-2009-7008154, 11 pages.
Response to European Office Action dated Jun. 28, 2011 for counterpart European Application No. 07843018.2, 5 pages.
Response to Singapore Office Action dated May 24, 2011 for counterpart Singapore Application No. 200901845-8, 10 pages.

Response to Australian Office Action dated Oct. 15, 2010 for counterpart Australia Application No. 2007299638, 20 pages.
Amendment before Examination for counterpart EP Application No. 07 843 016.2, dated Jun. 18, 2009, 8 pages.
Response to European Office Acfion for counterpart EP Application No. 07 843 018.2, dated Sep. 10, 2010, 10 pages.
European Office Action for counterpart EP Application No. 07 843 016.2, dated Feb. 24, 2011, 3 pages.
Response to Chinese Office Action for counterpart Chinese Patent Application No. 200780043385.8, dated Jul. 5, 2011, 5 pages.
Response to Russian Office Action for counterpart Russian Patent Application No. 2009115193, dated Aug. 20, 2010, 5 pages.
Response to Korean Office Action for counterpart Korean Patent Application No. 10-2009-7008154, dated Mar. 11, 2011, 5 pages.
Singapore Office Action for counterpart Singapore Patent Application No. 200901845-8, dated Dec. 30, 2010, 10 pages.
Response to Singapore Office Action for counterpart Singapore Patent Application No. 200901845-8, dated Sep. 2, 2010, 1 page.
Response to Singapore Office Action for counterpart Singapore Patent Application No. 200901845-8, dated Sep. 1, 2010, 12 pages.
Response to Singapore Office Action for counterpart Singapore Patent Application No. 200901845-8, dated Aug. 20, 2010, 5 pages.
Singapore Written Opinion for counterpart Singapore Patent Application No. 200901845-8, dated Apr. 15, 2010, 2 pages.
Second Office Action from counterpart Chinese Patent Application No. 200780043385.8 dated Feb. 14, 2012, 2 pages.
Indonesia instructions to Office Action dated Jun. 11, 2012; from counterpart Indonesia application No. WO00200802864.
Indonesia additional instructions to Office Action dated Jun. 15, 2012; from counterpart Indonesia application No. WO00200802864.
Korean instructions to Office Action dated Jun. 11, 2012; from counterpart Korean application No. 10-2009-7008154.
Korean Response to Office Action dated Jun. 21, 2012; from counterpart Korean application No. 10-2009-7008154.
Chinese Instructions to Third Office Action dated Jul. 16, 2012; from counterpart Chinese application No. 200780043385.8.
Chinese Response to Third Office Action dated Aug. 6, 2012; from counterpart Chinese application No. 200780043385.8.
EP Comments to ESR dated Jul. 24, 2012; from counterpart EP application No. 12 160 526.5.
European Extended Search Report dated May 12, 2012 from counterpart EP Application No. 12160526.5.
Chinese Response to Second Official Action dated Apr. 25, 2012 from counterpart Chinese Application No. 200780043385.8.
Chinese Third Official Action dated Jun. 11, 2012 from counterpart Chinese Application No. 200780043385.8.
Korean Office Action dated Apr. 20, 2012 from counterpart Korean Application No. 10-2009-7008154.
India Office Action dated Feb. 24, 2012 from counterpart India Application No. W-00200900722.
Canadian Response to Examiner's Report dated Apr. 18, 2012 from counterpart Canadian Application No. 2,663,860.
EP Further OA and Suggestion Drat dated Dec. 18, 2012; from EP counterpart Application No. 12 160 526.5.
Our Instructions to EP Further OA dated Dec. 18, 2012; from EP counterpart Application No. 12 160 526.5.
EP Response to Office Action dated Jan. 7, 2013; from EP counterpart Application No. 12 160 526.5.
CN 4th Office Action dated Nov. 4, 2012; from CN counterpart Application No. 200780043386.8.
Instructions to CN 4th Office Action dated Jan. 16, 2013; from CN counterpart Application No. 200780043386.8.
KR Office Action dated Oct. 16, 2013; from KR counterpart Application No. 10-2012-7015957.
Indonesia Response filed Jun. 22, 2012; from counterpart Indonesia application No. W-00 2009 00722.
EP Comments to Extended Search Report dated Dec. 18, 2012; from EP counterpart Application No. 12160526.5.
EP Response to Extended Search Report dated Dec. 20, 2012; from EP counterpart Application No. 12160526.5.
Chinese Fourth Office Action dated Nov. 4, 2012; from Chinese counterpart Application No. 200780043385.8.
Instructions to Chinese Fourth Office Action to associate dated Jan. 16, 2013; from Chinese counterpart Application No. 200780043385.8.
Chinese Response to 4th Office Action dated Jan. 20, 2013; from Chinese counterpart Application No. 200780043385.8.
Instructions to Korean Office Action dated Feb. 8, 2013; from Korean Divisional counterpart Application No. 10-2012-7015957.
Korean Response to Office Action dated Feb. 20, 2013; from from Korean Divisional counterpart Application No. 10-2012-7015957.

* cited by examiner

FIBRILLATED POLYOLEFIN FOAM

BACKGROUND OF DISCLOSURE

1. Field of the Disclosure

The present disclosure relates generally to the production of polyolefin foams for applications in absorbent materials.

2. Background Art

Absorbent materials are used in many personal care articles ranging from baby diapers to hygiene pads for adult incontinence and feminine needs. The efficacy of absorbent articles is dependent on several properties of the core absorbent material including high void volumes, hydrophilicity, wet resiliency, speed of absorption, and the ability to maintain void volume when wet. In diapers, for example, the absorbent core must quickly acquire fluids, distribute it in the void space, and act as a temporary reservoir until the super absorbent polymer (SAP) can absorb and hold the fluid.

The properties of absorbent materials are generally affected by the method with which they are deposited on their supporting surface. For example, wet laid materials generally suffer from high density due to the planar arrangement of the fibers. Air laid materials tend to have high bulk, but are limited in their stability and resiliency in addition to limitations of porosity. Traditional fluff pulp and creped tissue offer high void volumes and are hydrophilic, but collapse when wetted. The development of absorbent foams has proven promising in addressing some of these shortcomings.

Foams and foam materials, which can exhibit high absorbency properties, are generally made from low density elastomers, plastics, and other materials with various porosities. There are six basic types of foams and foam materials: open cellular, closed cellular, flexible, rigid, reticular, and syntactic. Open cellular foams have interconnected pores or cells and are suitable for filtration applications. Closed cellular foams do not have interconnected pores or cells, but are useful for buoyancy or flotation applications. Flexible foams can bend, flex or absorb impacts without cracking or delaminating. Reticular foams have a very open structure with a matrix consisting of an interconnecting network of thin material strands or struts. Rigid foams feature a matrix with very little or no flexibility. Syntactic foams consist of rigid microspheres or glass micro-balloons held together by a plastic or resin matrix.

Foams with varied properties described above are commonly found in personal care products. One method of generating foams is the introduction of air into an aqueous dispersion of polymer particles in the presence of foam stabilizing surfactants via a frothing process. Frothing may be continued until a desired foam density is obtained. At this point the foam may be laid on a substrate or conveyor belt for drying. An example of a polyolefin froth foam (PFF) made according to such a method is shown in FIGS. 1a and 1b, an SEM image of a cross section (FIG. 1a) and surface (FIG. 1b) of a prior art polyolefin froth foam. As shown in FIG. 1a these foams are open cell from surface to surface. That is, the foams have a continuous reticulated open cell morphology that includes small cells on the surface and larger cells toward the middle of the cross section depicting a sponge like morphology. The capillary pressure created by this type of morphology provides the foams with some of the fluid absorption properties desired for hygiene personal care products, such as insult absorption and distribution or wicking. However, limitations on the speed at which the fluid is absorbed (insult rate) exist for these foams. When an insult rate is too low, fluid may overflow the foam surface before all of the fluid insult is absorbed into the foam pad.

Additionally, because the capillary force holding the fluid in the small surface cells of the cellular foam is typically stronger than the osmotic absorption pressure of the SAP, the foam may retain at least a portion of the fluid, preventing absorption by the SAP. This results in an absorbent core having fluid available for rewetting skin when a load is placed on the core.

Another challenge in the formulation of frothed type foams is inconsistent and undesired foam collapse during the drying process, thus making the properties of the foam difficult to control. Fiber-laden foams have proven utility in reducing the degree of collapse during the drying process. U.S. Pat. Nos. 6,261,679 and 6,603,054, both issued to Chen et al., describe methods of making absorbent materials having a base material of cellulosic or other similar fibers. Both the '679 patent and the '054 patent disclose that these hydrophilic fibers should comprise the predominant structural component of the absorbent foam, comprising up to 98% by weight of the foam's mass. A polymer bonding agent that acts as a glue for the strut like fibers largely comprises the remaining 2-10% mass of the foam.

Accordingly, there exists a continuing need for absorbent articles with increased rates of absorption. In the process, it is desirable to maintain high void volumes and increase the surface openings to reduce capillary retention of fluid.

SUMMARY OF DISCLOSURE

In one aspect, embodiments disclosed herein relate to a method for generating a thermoplastic foam from an aqueous dispersion, the aqueous dispersion comprising a thermoplastic resin, water, and a dispersion stabilizing agent, the method including: adding at least one froth stabilizing surfactant to the aqueous dispersion to form a mixture; adding a fiber to the mixture; and frothing the mixture to create a froth, removing at least a portion of the water in the froth to create a foam, wherein the foam generated has a non-cellular fibrillated morphology.

In another aspect, embodiments disclosed herein relate to foams having a thermoplastic-based, fibrillated, non-cellular structure, wherein the foam has an average density of about 0.02 g/cm$^3$ to about 0.07 g/cm$^3$. In certain embodiments, the foam may be used in an absorbent article, such as a baby diaper, a feminine hygiene product, an adult incontinence product, a wound dressing pad, a surgical sponge, a medical garment, a surgical drapery, a wiping towel, a wiping sponge, and a food packaging pad.

Other aspects and advantages of the disclosure will become apparent from the following description and attached claims.

DETAILED DESCRIPTION

Embodiments of the disclosure relate to absorbent materials for use in personal care absorbent articles and methods for making absorbent materials. In particular, certain embodiments relate to foams formed with thermoplastic resin particles and thermoplastic fibers. In particular, embodiments relate to foams formed from aqueous dispersions of polyolefin particles that are combined with polyolefin fibers. In the following description, numerous details are set forth to provide an understanding of the present disclosure. However, it will be understood by those skilled in the art that the present disclosure may be practiced without these details and that numerous variations or modifications from the described embodiments may be possible.

One embodiment of the disclosure comprises a method for generating thermoplastic foams. The absorbent structures of the present disclosure may be formed by mixing thermoplastic fibers with an aqueous dispersion, wherein the aqueous dispersion may include a thermoplastic resin, water, and a stabilizing agent. The mixture of the fibers and the aqueous dispersion may be frothed to create a froth, which may be subsequently dried to remove at least a portion of the water, forming a foam.

As used herein, the term "frothing" or "frothed" refers to a process of incorporating substantial volumes of air, or other gas, in a liquid where, in some embodiments, at least 80 volume percent of the frothed material consists of the gaseous component. In other embodiments, at least 85 volume percent of the frothed material consists of the gaseous component; and at least 90 volume percent in yet other embodiments. The liquid may be a molecular solution, a micellar solution, or a dispersion in an aqueous or organic medium. In general the frothed liquid is created by mechanical methods such as high shear mixing under atmospheric conditions or optionally injecting gas into the system while mixing. The term "froth" as used herein refers to an liquid which has been frothed, as described above, before drying or removing the liquid medium. As used herein, drying and removing may be used interchangeably, and may include thermal and/or mechanical removal of the liquid medium.

Figure 2:
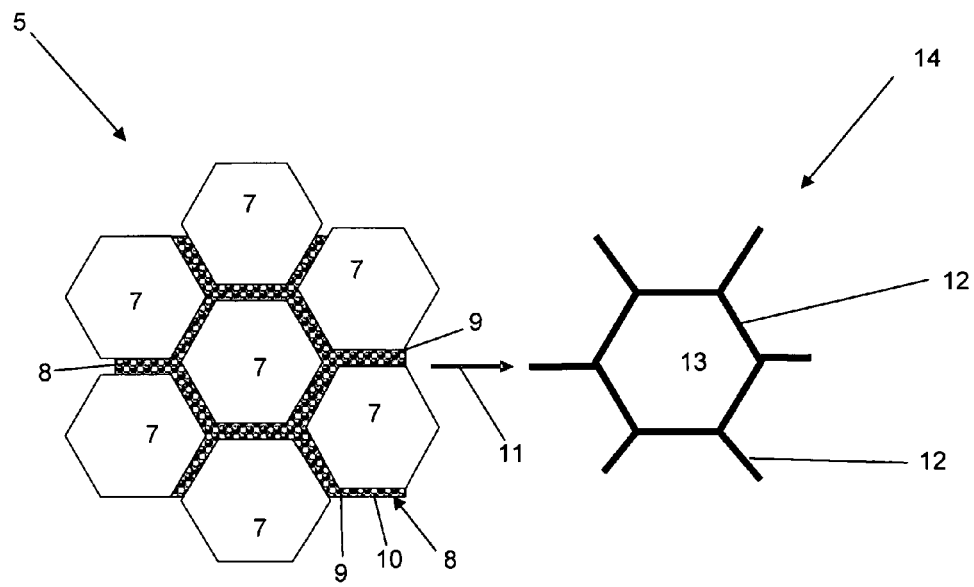
FIG. 2 illustrates formation of a foam from a froth in accordance with embodiments disclosed herein.

The term "foam" as used herein refers to a resilient structure formed by removing a portion of the liquid medium from a froth, e.g. at least a portion, a substantial portion, or all of the liquid medium may be removed. The formation of a foam from a froth in accordance with embodiments disclosed herein is illustrated in FIG. 2. A froth 5 may include pockets of vapor 7 within dispersion 8, where the dispersion 8 includes polymer particles 10 in a liquid medium 9. When the liquid medium 9 is removed from the froth 5 during a drying or removing process 11, the polymer particles 10 coalesce and melt together creating interconnected film or struts 12 around the entrapped vapor bubbles 13, giving stability to the resulting structure 14. Film formation may depend upon variables including the melting point of polymers within the froth, the rate of removal (i.e., evaporation rate) of the liquid medium, and overall froth composition, among others. For example, as water is removed from a froth formed from an aqueous dispersion, polymers contained in the dispersion may coalesce, forming a film, giving structure and resiliency to the resulting foam. In some embodiments, a foam may be formed where the amount of residual liquid ranges from 0 to 20 weight percent; 0 to 10 weight percent in other embodiments; and 0 to 8 percent in yet other embodiments.

Aqueous Dispersion

More generally, embodiments of the present disclosure relate to aqueous dispersions and compounds made from aqueous dispersions that are useful in forming frothed foams. These frothed foams may be useful, for example, in liquid absorbency applications. Dispersions used in embodiments of the present disclosure comprise water, (A) at least one thermoplastic resin, and (B) a stabilizing agent. These are discussed in more detail below.

Thermoplastic Resin

The thermoplastic resin (A) included in embodiments of the aqueous dispersion of the present disclosure is a resin that is not readily dispersible in water by itself. The term "resin," as used herein, should be construed to include synthetic polymers or chemically modified natural resins.

Resins used herein may include elastomers and blends of olefin polymers. In some embodiments, the thermoplastic resin is a semicrystalline resin. The term "semicrystalline" is intended to identify those resins that possess at least one endotherm when subjected to standard differential scanning calorimetry (DSC) evaluation. Some semicrystalline polymers exhibit a DSC endotherm that exhibits a relatively gentle slope as the scanning temperature is increased past the final endotherm maximum. This reflects a polymer of broad melting range rather than a polymer having what is generally considered to be a sharp melting point. Some polymers useful in the dispersions of the disclosure have a single melting point while other polymers have more than one melting point.

In some polymers one or more of the melting points may be sharp such that all or a portion of the polymer melts over a fairly narrow temperature range, such as a few degrees centigrade. In other embodiments, the polymer may exhibit broad melting characteristics over a range of about 20° C. In yet other embodiments, the polymer may exhibit broad melting characteristics over a range of greater than 50° C.

Examples of the thermoplastic resin (A) which may be used in the present disclosure include homopolymers and copolymers (including elastomers) of an alpha-olefin such as ethylene, propylene, 1-butene, 3-methyl-1-butene, 4-methyl-1-pentene, 3-methyl-1-pentene, 1-heptene, 1-hexene, 1-octene, 1-decene, and 1-dodecene, as typically represented by polyethylene, polypropylene, poly-1-butene, poly-3-methyl-1-butene, poly-3-methyl-1-pentene, poly-4-methyl-1-pentene, ethylene-propylene copolymer, ethylene-1-butene copolymer, and propylene-1-butene copolymer; copolymers (including elastomers) of an alpha-olefin with a conjugated or non-conjugated diene, as typically represented by ethylene-butadiene copolymer and ethylene-ethylidene norbornene copolymer; and polyolefins (including elastomers) such as copolymers of two or more alpha-olefins with a conjugated or non-conjugated diene, as typically represented by ethylene-propylene-butadiene copolymer, ethylene-propylene-dicyclopentadiene copolymer, ethylene-propylene-1,5-hexadiene copolymer, and ethylene-propylene-ethylidene norbornene copolymer; ethylene-vinyl compound copolymers such as ethylene-vinyl acetate copolymer, ethylene-vinyl alcohol copolymer, ethylene-vinyl chloride copolymer, ethylene acrylic acid or ethylene-(meth)acrylic acid copolymers, and ethylene-(meth)acrylate copolymer; styrenic copolymers (including elastomers) such as polystyrene, ABS, acrylonitrile-styrene copolymer, α-methylstyrene-styrene copolymer, styrene vinyl alcohol, styrene acrylates such as styrene methylacrylate, styrene butyl acrylate, styrene butyl methacrylate, and styrene butadienes and crosslinked styrene polymers; and styrene block copolymers (including elastomers) such as styrene-butadiene copolymer and hydrate thereof, and styrene-isoprene-styrene tri-block copolymer; polyvinyl compounds such as polyvinyl chloride, polyvinylidene chloride, vinyl chloride-vinylidene chloride copolymer, polymethyl acrylate, and polymethyl methacrylate; polyamides such as nylon 6, nylon 6,6, and nylon 12; thermoplastic polyesters such as polyethylene terephthalate and polybutylene terephthalate; polycarbonate, polyphenylene oxide, and the like; and glassy hydrocarbon-based resins, including poly-dicyclopentadiene polymers and related polymers (copolymers, terpolymers); saturated mono-olefins such as vinyl acetate, vinyl propionate and vinyl butyrate and the like; vinyl esters such as esters of monocarboxylic acids, including methyl acrylate, ethyl acrylate, n-butylacrylate, isobutyl acrylate, dodecyl acrylate, n-octyl acrylate, phenyl acrylate, methyl methacrylate, ethyl methacrylate, and butyl methacrylate and the like; acrylonitrile, methacrylonitrile, acrylamide, mixtures thereof; resins produced by ring opening metathesis and cross metathesis polymerization and the like. These resins may be used either alone or in combinations of two or more In one particular embodiment, the thermoplastic resin may comprise an alpha-olefin interpolymer of ethylene with a comonomer comprising an alkene, such as 1-octene. The ethylene and octene copolymer may be present alone or in combination with another thermoplastic resin, such as ethylene-acrylic acid copolymer. When present together, the weight ratio between the ethylene and octene copolymer and the ethylene-acrylic acid copolymer may range from about 1:10 to about 10:1, such as from about 3:2 to about 2:3. The polymeric resin, such as the ethylene-octene copolymer, may have a crystallinity of less than about 50%, such as less than about 25%. In some embodiments, the crystallinity of the polymer may range from 5 to 35 percent. In other embodiments, the crystallinity may range from 7 to 20 percent.

Embodiments disclosed herein may also include a polymeric component that may include at least one multi-block olefin interpolymer. Suitable multi-block olefin interpolymers may include those described in U.S. Provisional Patent Application No. 60/818,911, for example. The term "multi-block copolymer" or refers to a polymer comprising two or more chemically distinct regions or segments (referred to as "blocks") preferably joined in a linear manner, that is, a polymer comprising chemically differentiated units which are joined end-to-end with respect to polymerized ethylenic functionality, rather than in pendent or grafted fashion. In certain embodiments, the blocks differ in the amount or type of comonomer incorporated therein, the density, the amount of crystallinity, the crystallite size attributable to a polymer of such composition, the type or degree of tacticity (isotactic or syndiotactic), regio-regularity or regio-irregularity, the amount of branching, including long chain branching or hyper-branching, the homogeneity, or any other chemical or physical property. The multi-block copolymers are characterized by unique distributions of polydispersity index (PDI or $M_w/M_n$), block length distribution, and/or block number distribution due to the unique process making of the copolymers. More specifically, when produced in a continuous process, embodiments of the polymers may possess a PDI ranging from about 1.7 to about 8; from about 1.7 to about 3.5 in other embodiments; from about 1.7 to about 2.5 in other embodiments; and from about 1.8 to about 2.5 or from about 1.8 to about 2.1 in yet other embodiments. When produced in a batch or semi-batch process, embodiments of the polymers may possess a PDI ranging from about 1.0 to about 2.9; from about 1.3 to about 2.5 in other embodiments; from about 1.4 to about 2.0 in other embodiments; and from about 1.4 to about 1.8 in yet other embodiments.

One example of the multi-block olefin interpolymer is an ethylene/α-olefin block interpolymer. Another example of the multi-block olefin interpolymer is a propylene/α-olefin interpolymer. The following description focuses on the interpolymer as having ethylene as the majority monomer, but applies in a similar fashion to propylene-based multi-block interpolymers with regard to general polymer characteristics.

The ethylene/α-olefin multi-block copolymers may comprise ethylene and one or more co-polymerizable α-olefin comonomers in polymerized form, characterized by multiple (i.e., two or more) blocks or segments of two or more polymerized monomer units differing in chemical or physical properties (block interpolymer). In some embodiments, the copolymer is a multi-block interpolymer. In some embodiments, the multi-block interpolymer may be represented by the following formula:

$$(AB)_n$$

where n is at least 1, and in various embodiments n is an integer greater than 1, such as 2, 3, 4, 5, 10, 15, 20, 30, 40, 50, 60, 70, 80, 90, 100, or higher; "A" represents a hard block or segment; and "B" represents a soft block or segment. Preferably, A's and B's are linked in a linear fashion, not in a branched or a star fashion. "Hard" segments refer to blocks of polymerized units in which ethylene is present in an amount greater than 95 weight percent in some embodiments, and in other embodiments greater than 98 weight percent. In other words, the comonomer content in the hard segments is less than 5 weight percent in some embodiments, and in other embodiments, less than 2 weight percent of the total weight of the hard segments. In some embodiments, the hard segments comprise all or substantially all ethylene. "Soft" segments, on the other hand, refer to blocks of polymerized units in which the comonomer content is greater than 5 weight percent of the total weight of the soft segments in some embodiments, greater than 8 weight percent, greater than 10 weight percent, or greater than 15 weight percent in various other embodiments. In some embodiments, the comonomer content in the soft segments may be greater than 20 weight percent, greater than 25 eight percent, greater than 30 weight percent, greater than 35 weight percent, greater than 40 weight percent, greater than 45 weight percent, greater than 50 weight percent, or greater than 60 weight percent in various other embodiments.

In some embodiments, A blocks and B blocks are randomly distributed along the polymer chain. In other words, the block copolymers do not have a structure like:

*AAA-AA-BBB-BB*

In other embodiments, the block copolymers do not have a third block. In still other embodiments, neither block A nor block B comprises two or more segments (or sub-blocks), such as a tip segment.

The multi-block interpolymers may be characterized by an average block index, ABI, ranging from greater than zero to about 1.0 and a molecular weight distribution, $M_w/M_n$, greater than about 1.3. The average block index, ABI, is the weight average of the block index ("BI") for each of the polymer fractions obtained in preparative TREF from 20° C. and 110° C., with an increment of 5° C.:

$$ABI=\Sigma(w_iBI_i)$$

where $BI_i$ is the block index for the $i^{th}$ fraction of the multi-block interpolymer obtained in preparative TREF, and $w_i$ is the weight percentage of the $i^{th}$ fraction.

Similarly, the square root of the second moment about the mean, hereinafter referred to as the second moment weight average block index, may be defined as follows:

$$2^{nd} \text{ moment weight average } BI = \sqrt{\frac{\sum(w_i(BI_i - ABI)^2)}{\frac{(N-1)\sum w_i}{N}}}$$

For each polymer fraction, BI is defined by one of the two following equations (both of which give the same BI value):

$$BI = \frac{1/T_X - 1/T_{XO}}{1/T_A - 1/T_{AB}} \text{ or } BI = -\frac{LnP_X - LnP_{XO}}{LnP_A - LnP_{AB}}$$

where $T_X$ is the analytical temperature rising elution fractionation (ATREF) elution temperature for the $i^{th}$ fraction (preferably expressed in Kelvin), $P_X$ is the ethylene mole fraction for the $i^{th}$ fraction, which may be measured by NMR or IR as described below. $P_{AB}$ is the ethylene mole fraction of the whole ethylene/α-olefin interpolymer (before fractionation), which also may be measured by NMR or IR. $T_A$ and $P_A$ are the ATREF elution temperature and the ethylene mole fraction for pure "hard segments" (which refer to the crystalline segments of the interpolymer). As an approximation or for polymers where the "hard segment" composition is unknown, the $T_A$ and $P_A$ values are set to those for high density polyethylene homopolymer.

$T_{AB}$ is the ATREF elution temperature for a random copolymer of the same composition (having an ethylene mole fraction of $P_{AB}$) and molecular weight as the multi-block interpolymer. $T_{AB}$ may be calculated from the mole fraction of ethylene (measured by NMR) using the following equation:

$$Ln P_{AB} = \alpha/T_{AB} + \beta$$

where α and β are two constants which may be determined by a calibration using a number of well characterized preparative TREF fractions of a broad composition random copolymer and/or well characterized random ethylene copolymers with narrow composition. It should be noted that α and β may vary from instrument to instrument. Moreover, one would need to create an appropriate calibration curve with the polymer composition of interest, using appropriate molecular weight ranges and comonomer type for the preparative TREF fractions and/or random copolymers used to create the calibration. There is a slight molecular weight effect. If the calibration curve is obtained from similar molecular weight ranges, such effect would be essentially negligible. In some embodiments, random ethylene copolymers and/or preparative TREF fractions of random copolymers satisfy the following relationship:

$$Ln P = -237.83/T_{ATREF} + 0.639$$

The above calibration equation relates the mole fraction of ethylene, P, to the analytical TREF elution temperature, $T_{ATREF}$, for narrow composition random copolymers and/or preparative TREF fractions of broad composition random copolymers. $T_{XO}$ is the ATREF temperature for a random copolymer of the same composition and having an ethylene mole fraction of $P_X$. $T_{XO}$ may be calculated from $LnP_X = \alpha/T_{XO} + \beta$. Conversely, $P_{XO}$ is the ethylene mole fraction for a random copolymer of the same composition and having an ATREF temperature of $T_X$, which may be calculated from $Ln P_{XO} = \alpha/T_X + \beta$.

Once the block index (BI) for each preparative TREF fraction is obtained, the weight average block index, ABI, for the whole polymer may be calculated. In some embodiments, ABI is greater than zero but less than about 0.4 or from about 0.1 to about 0.3. In other embodiments, ABI is greater than about 0.4 and up to about 1.0. In yet other embodiments, ABI should be in the range of from about 0.4 to about 0.7, from about 0.5 to about 0.7, or from about 0.6 to about 0.9. In some embodiments, ABI is in the range of from about 0.3 to about 0.9, from about 0.3 to about 0.8, or from about 0.3 to about 0.7, from about 0.3 to about 0.6, from about 0.3 to about 0.5, or from about 0.3 to about 0.4. In other embodiments, ABI is in the range of from about 0.4 to about 1.0, from about 0.5 to about 1.0, or from about 0.6 to about 1.0, from about 0.7 to about 1.0, from about 0.8 to about 1.0, or from about 0.9 to about 1.0.

Another characteristic of the multi-block interpolymer is that the interpolymer may comprise at least one polymer fraction which may be obtained by preparative TREF, wherein the fraction has a block index greater than about 0.1 and up to about 1.0 and the polymer having a molecular weight distribution, $M_w/M_n$, greater than about 1.3. In some embodiments, the polymer fraction has a block index greater than about 0.6 and up to about 1.0, greater than about 0.7 and up to about 1.0, greater than about 0.8 and up to about 1.0, or greater than about 0.9 and up to about 1.0. In other embodiments, the polymer fraction has a block index greater than about 0.1 and up to about 1.0, greater than about 0.2 and up to about 1.0, greater than about 0.3 and up to about 1.0, greater than about 0.4 and up to about 1.0, or greater than about 0.4 and up to about 1.0. In still other embodiments, the polymer fraction has a block index greater than about 0.1 and up to about 0.5, greater than about 0.2 and up to about 0.5, greater than about 0.3 and up to about 0.5, or greater than about 0.4 and up to about 0.5. In yet other embodiments, the polymer fraction has a block index greater than about 0.2 and up to about 0.9, greater than about 0.3 and up to about 0.8, greater than about 0.4 and up to about 0.7, or greater than about 0.5 and up to about 0.6.

Ethylene α-olefin multi-block interpolymers used in embodiments disclosed herein may be interpolymers of ethylene with at least one $C_3$-$C_{20}$ α-olefin. The interpolymers may further comprise $C_4$-$C_{18}$ diolefin and/or alkenylbenzene. Suitable unsaturated comonomers useful for polymerizing with ethylene include, for example, ethylenically unsaturated monomers, conjugated or non-conjugated dienes, polyenes, alkenylbenzenes, etc. Examples of such comonomers include $C_3$-$C_{20}$ α-olefins such as propylene, isobutylene, 1-butene, 1-hexene, 1-pentene, 4-methyl-1-pentene, 1-heptene, 1-octene, 1-nonene, 1-decene, and the like. In certain embodiments, the α-olefins may be 1-Butene or 1-octene. Other suitable monomers include styrene, halo- or alkyl-substituted styrenes, vinylbenzocyclobutane, 1,4-hexadiene, 1,7-octadiene, and naphthenics (such as cyclopentene, cyclohexene, and cyclooctene, for example).

The multi-block interpolymers disclosed herein may be differentiated from conventional, random copolymers, physical blends of polymers, and block copolymers prepared via sequential monomer addition, fluxional catalysts, and anionic or cationic living polymerization techniques. In particular, compared to a random copolymer of the same monomers and monomer content at equivalent crystallinity or modulus, the interpolymers have better (higher) heat resistance as measured by melting point, higher TMA penetration temperature, higher high-temperature tensile strength, and/or higher high-temperature torsion storage modulus as determined by dynamic mechanical analysis. Properties of infill may benefit from the use of embodiments of the multi-block interpolymers, as compared to a random copolymer containing the same monomers and monomer content, the multi-block interpolymers have lower compression set, particularly at elevated temperatures, lower stress relaxation, higher creep resistance, higher tear strength, higher blocking resistance, faster setup due to higher crystallization (solidification) temperature, higher recovery (particularly at elevated temperatures), better abrasion resistance, higher retractive force, and better oil and filler acceptance.

Other olefin interpolymers include polymers comprising monovinylidene aromatic monomers including styrene, o-methyl styrene, p-methyl styrene, t-butylstyrene, and the like. In particular, interpolymers comprising ethylene and styrene may be used. In other embodiments, copolymers comprising ethylene, styrene and a $C_3$-$C_{20}$ α olefin, optionally comprising a $C_4$-$C_{20}$ diene, may be used.

Suitable non-conjugated diene monomers may include straight chain, branched chain or cyclic hydrocarbon diene having from 6 to 15 carbon atoms. Examples of suitable non-conjugated dienes include, but are not limited to, straight chain acyclic dienes, such as 1,4-hexadiene, 1,6-octadiene, 1,7-octadiene, 1,9-decadiene, branched chain acyclic dienes, such as 5-methyl-1,4-hexadiene; 3,7-dimethyl-1,6-octadiene; 3,7-dimethyl-1,7-octadiene and mixed isomers of dihydromyricene and dihydroocinene, single ring alicyclic dienes, such as 1,3-cyclopentadiene; 1,4-cyclohexadiene; 1,5-cyclooctadiene and 1,5-cyclododecadiene, and multi-ring alicyclic fused and bridged ring dienes, such as tetrahydroindene, methyl tetrahydroindene, dicyclopentadiene, bicyclo-(2,2,1)-hepta-2,5-diene; alkenyl, alkylidene, cycloalkenyl and cycloalkylidene norbornenes, such as 5-methylene-2-norbornene (MNB); 5-propenyl-2-norbornene, 5-isopropylidene-2-norbornene, 5-(4-cyclopentenyl)-2-norbornene, 5-cyclohexylidene-2-norbornene, 5-vinyl-2-norbornene, and norbornadiene. Of the dienes typically used to prepare EPDMs, the particularly preferred dienes are 1,4-hexadiene (HD), 5-ethylidene-2-norbornene (ENB), 5-vinylidene-2-norbornene (VNB), 5-methylene-2-norbornene (MNB), and dicyclopentadiene (DCPD).

One class of desirable polymers that may be used in accordance with embodiments disclosed herein includes elastomeric interpolymers of ethylene, a $C_3$-$C_{20}$ α-olefin, especially propylene, and optionally one or more diene monomers. Preferred α-olefins for use in this embodiment are designated by the formula $CH_2$=$CHR^*$, where $R^*$ is a linear or branched alkyl group of from 1 to 12 carbon atoms. Examples of suitable α-olefins include, but are not limited to, propylene, isobutylene, 1-butene, 1-pentene, 1-hexene, 4-methyl-1-pentene, and 1-octene. A particularly preferred α-olefin is propylene. The propylene based polymers are generally referred to in the art as EP or EPDM polymers. Suitable dienes for use in preparing such polymers, especially multi-block EPDM type polymers include conjugated or non-conjugated, straight or branched chain-, cyclic- or polycyclic-dienes comprising from 4 to 20 carbons. Preferred dienes include 1,4-pentadiene, 1,4-hexadiene, 5-ethylidene-2-norbornene, dicyclopentadiene, cyclohexadiene, and 5-butylidene-2-norbornene. A particularly preferred diene is 5-ethylidene-2-norbornene.

As one suitable type of resin, the esterification products of a di- or poly-carboxylic acid and a diol comprising a diphenol may be used. These resins are illustrated in U.S. Pat. No. 3,590,000, which is incorporated herein by reference. Other specific examples of resins include styrene/methacrylate copolymers, and styrene/butadiene copolymers; suspension polymerized styrene butadienes; polyester resins obtained from the reaction of bisphenol A and propylene oxide followed by the reaction of the resulting product with fumaric acid; and branched polyester resins resulting from the reaction of dimethylterphthalate, 1,3-butanediol, 1,2-propanediol, and pentaerythritol, styrene acrylates, and mixtures thereof.

Further, specific embodiments of the present disclosure may employ ethylene-based polymers, propylene-based polymers, propylene-ethylene copolymers, and styrenic copolymers as one component of a composition. Other embodiments of the present disclosure may use polyester resins, including those containing aliphatic diols such as UNOXOL 3,4 diol, available from The Dow Chemical Company (Midland, Mich.).

In select embodiments, the thermoplastic resin is formed from ethylene-alpha olefin copolymers or propylene-alpha olefin copolymers. In particular, in select embodiments, the thermoplastic resin includes one or more non-polar polyolefins.

In specific embodiments, polyolefins such as polypropylene, polyethylene, copolymers thereof, and blends thereof, as well as ethylene-propylene-diene terpolymers, may be used. In some embodiments, preferred olefinic polymers include homogeneous polymers, as described in U.S. Pat. No. 3,645,992 issued to Elston; high density polyethylene (HDPE), as described in U.S. Pat. No. 4,076,698 issued to Anderson; heterogeneously branched linear low density polyethylene (LLDPE); heterogeneously branched ultra low linear density polyethylene (ULDPE); homogeneously branched, linear ethylene/alpha-olefin copolymers; homogeneously branched, substantially linear ethylene/alpha-olefin polymers, which can be prepared, for example, by processes disclosed in U.S. Pat. Nos. 5,272,236 and 5,278,272, the disclosures of which are incorporated herein by reference; and high pressure, free radical polymerized ethylene polymers and copolymers such as low density polyethylene (LDPE) or ethylene vinyl acetate polymers (EVA).

Polymer compositions, and blends thereof, described in U.S. Pat. Nos. 6,566,446, 6,538,070, 6,448,341, 6,316,549, 6,111,023, 5,869,575, 5,844,045, or 5,677,383, each of which is incorporated herein by reference in its entirety, may also be suitable in some embodiments. In some embodiments, the blends may include two different Ziegler-Natta polymers. In other embodiments, the blends may include blends of a Ziegler-Natta polymer and a metallocene polymer. In still other embodiments, the polymer used herein may be a blend of two different metallocene polymers. In other embodiments, single site catalyst polymers may be used.

In some embodiments, the polymer is a propylene-based copolymer or interpolymer. In some particular embodiments, the propylene/ethylene copolymer or interpolymer is characterized as having substantially isotactic propylene sequences. The term "substantially isotactic propylene sequences" and similar terms mean that the sequences have an isotactic triad (mm) measured by $^{13}$C NMR of greater than about 0.85 in one embodiment; greater than about 0.90 in another embodiment; greater than about 0.92 in another embodiment; and greater than about 0.93 in yet another embodiment. Isotactic triads are well-known in the art and are described in, for example, U.S. Pat. No. 5,504,172 and WO 00/01745, which refer to the isotactic sequence in terms of a triad unit in the copolymer molecular chain determined by $^{13}$C NMR spectra.

The olefin polymers, copolymers, interpolymers, and multi-block interpolymers may be functionalized by incorporating at least one functional group in its polymer structure. Exemplary functional groups may include, for example, ethylenically unsaturated mono- and di-functional carboxylic acids, ethylenically unsaturated mono- and di-functional carboxylic acid anhydrides, salts thereof and esters thereof. Such functional groups may be grafted to an olefin polymer, or it may be copolymerized with ethylene and an optional additional comonomer to form an interpolymer of ethylene, the functional comonomer and optionally other comonomer(s). Means for grafting functional groups onto polyethylene are described for example in U.S. Pat. Nos. 4,762,890, 4,927,888, and 4,950,541, the disclosures of which are incorporated herein by reference in their entirety. One particularly useful functional group is maleic anhydride.

The amount of the functional group present in the functional polymer may vary. The functional group may be present in an amount of at least about 1.0 weight percent in some embodiments; at least about 5 weight percent in other embodiments; and at least about 7 weight percent in yet other embodiments. The functional group may be present in an amount less than about 40 weight percent in some embodiments; less than about 30 weight percent in other embodiments; and less than about 25 weight percent in yet other embodiments.

In other particular embodiments, the thermoplastic resin may be ethylene vinyl acetate (EVA) based polymers. In other embodiments, the thermoplastic resin may be ethylene-methyl acrylate (EMA) based polymers. In other particular embodiments, the ethylene-alpha olefin copolymer may be ethylene-butene, ethylene-hexene, or ethylene-octene copolymers or interpolymers. In other particular embodiments, the propylene-alpha olefin copolymer may be a propylene-ethylene or a propylene-ethylene-butene copolymer or interpolymer.

In certain embodiments, the thermoplastic resin may be an ethylene-octene copolymer or interpolymer having a density between 0.857 and 0.911 g/cc and melt index (190° C. with 2.16 kg weight) from 0.1 to 100 g/10 min. In other embodiments, the ethylene-octene copolymers may have a density between 0.863 and 0.902 g/cc and melt index (190° C. with 2.16 kg weight) from 0.8 to 35 g/10 min. The ethylene-octene copolymer or interpolymer may incorporate 20-45% octene by weight of ethylene and octene.

In certain embodiments, the thermoplastic resin may be a propylene-ethylene copolymer or interpolymer having an ethylene content between 5 and 20% by weight and a melt flow rate (230° C. with 2.16 kg weight) from 0.5 to 300 g/10 min. In other embodiments, the propylene-ethylene copolymer or interpolymer may have an ethylene content between 9 and 12% by weight and a melt flow rate (230° C. with 2.16 kg weight) from 1 to 100 g/10 min.

In certain other embodiments, the thermoplastic resin may be a low density polyethylene having a density between 0.911 and 0.925 g/cc and melt index (190° C. with 2.16 kg weight) from 0.1 to 100 g/10 min.

In some embodiments, the thermoplastic resin may have a crystallinity of less than 50 percent. In other embodiments, the crystallinity of the resin may be from 5 to 35 percent. In yet other embodiments, the crystallinity may range from 7 to 20 percent.

In some embodiments, the thermoplastic resin is a semi-crystalline polymer and may have a melting point of less than 110° C. In other embodiments, the melting point may be from 25 to 100° C. In yet other embodiments, the melting point may be between 40 and 85° C.

In some embodiments, the thermoplastic resin is a glassy polymer and may have a glass transition temperature of less than 110° C. In other embodiments, the glass transition temperature may be from 20 to 100° C. In yet other embodiments, the glass transition temperature may be from 50 to 75° C.

In certain embodiments, the thermoplastic resin may have a weight average molecular weight greater than 10,000 g/mole. In other embodiments, the weight average molecular weight may be from 20,000 to 150,000 g/mole; in yet other embodiments, from 50,000 to 100,000 g/mole.

The one or more thermoplastic resins may be contained within the aqueous dispersion in an amount from about 1% by weight to about 96% by weight polymer solids. For instance, the thermoplastic resin may be present in the aqueous dispersion in an amount from about 10% by weight to about 60% by weight in one embodiment, and about 20% to about 50% by weight in another embodiment.

Stabilizing Agent

Embodiments of the present disclosure use a stabilizing agent to promote the formation of a stable dispersion or emulsion. In selected embodiments, the stabilizing agent may be a surfactant, a polymer (different from the base polymer detailed above), or mixtures thereof. In other embodiments, the resin is a self-stabilizer, so that an additional exogenous stabilizing agent may not be necessary. For example, a self-stabilizing system may include a partially hydrolyzed polyester, where by combining polyester with an aqueous base, a polyester resin and surfactant-like stabilizer molecule may be produced. In particular, the stabilizing agent may be used as a dispersant, a surfactant for frothing the foam, or may serve both purposes. In addition, one or more stabilizing agents may be used in combination.

In certain embodiments, the stabilizing agent may be a polar polymer, having a polar group as either a comonomer or grafted monomer. In preferred embodiments, the stabilizing agent may include one or more polar polyolefins, having a polar group as either a comonomer or grafted monomer. Typical polymers include ethylene-acrylic acid (EAA) and ethylene-methacrylic acid copolymers, such as those available under the trademarks PRIMACOR™ (trademark of The Dow Chemical Company), NUCREL™ (trademark of E.I. DuPont de Nemours), and ESCOR™ (trademark of Exxon-Mobil) and described in U.S. Pat. Nos. 4,599,392, 4,988,781, and 5,938,437, each of which is incorporated herein by reference in its entirety. Other suitable polymers include ethylene ethyl acrylate (EEA) copolymer, ethylene methyl methacrylate (EMMA), and ethylene butyl acrylate (EBA). Other ethylene-carboxylic acid copolymer may also be used. Those having ordinary skill in the art will recognize that a number of other useful polymers may also be used.

If the polar group of the polymer is acidic or basic in nature, the stabilizing polymer may be partially or fully neutralized with a neutralizing agent to form the corresponding salt. In certain embodiments, neutralization of the stabilizing agent, such as a long chain fatty acid or EAA, may be from 25 to 200% on a molar basis; from 50 to 110% on a molar basis in other embodiments. For example, for EAA, the neutralizing agent is a base, such as ammonium hydroxide or potassium hydroxide, for example. Other neutralizing agents can include lithium hydroxide or sodium hydroxide, for example. Those having ordinary skill in the art will appreciate that the selection of an appropriate neutralizing agent depends on the specific composition formulated, and that such a choice is within the knowledge of those of ordinary skill in the art.

Other stabilizing agents that may be used include long chain fatty acids or fatty acid salts having from 12 to 60 carbon atoms. In other embodiments, the long chain fatty acid or fatty acid salt may have from 12 to 40 carbon atoms.

Additional stabilizing agents that may be useful in the practice of the present disclosure include cationic surfactants, anionic surfactants, or non-ionic surfactants. Examples of anionic surfactants include sulfonates, carboxylates, and phosphates. Examples of cationic surfactants include quaternary amines. Examples of non-ionic surfactants include block copolymers containing ethylene oxide and silicone surfactants. Surfactants useful as a stabilizing agent may be either external surfactants or internal surfactants. External surfactants are surfactants that do not become chemically reacted into the polymer during dispersion preparation. Examples of external surfactants useful herein include salts of dodecyl benzene sulfonic acid and lauryl sulfonic acid salt. Internal surfactants are surfactants that do become chemically reacted into the polymer during dispersion preparation. An example of an internal surfactant useful herein includes 2,2-dimethylol propionic acid and its salts.

In particular embodiments, the dispersing agent or stabilizing agent may be used in an amount ranging from greater than zero to about 60% by weight based on the amount of thermoplastic resin (or thermoplastic resin mixture) used. For example, long chain fatty acids or salts thereof may be used from 0.5 to 10% by weight based on the amount of thermoplastic resin. In other embodiments, ethylene-acrylic acid or ethylene-methacrylic acid copolymers may be used in an amount from 0.5 to 60% by weight based on the amount of the thermoplastic resin. In yet other embodiments, sulfonic acid salts may be used in an amount from 0.5 to 10% by weight based on the amount of thermoplastic resin.

As discussed above, more than one stabilizing agent may be used, and combinations may be used as a dispersant and as a surfactant, for example.

Dispersants

In one embodiment, the aqueous dispersion may include dispersant in an amount of more than about 1% by weight of the aqueous dispersion; more than about 2% in another embodiment; and more than about 3% in yet another embodiment. In another embodiment, the aqueous dispersion may include a dispersant agent in an amount less than about 10% by weight of the aqueous dispersion; less than about 8% in another embodiment; and less than 5% in yet another embodiment.

Suitable dispersants for the polyolefin resin may include salts of fatty acid(s) of carbon chain length of greater than 12 in some embodiments, and from 18 to 36 carbon atoms in other embodiments. The salts may be alkali metal or ammonium salts of the fatty acid, prepared by neutralization of the acid with the corresponding base, e.g., NaOH, KOH, and $NH_4OH$. These salts may be formed in situ in the dispersion step, as described more fully below. The appropriate fatty acid dispersant may be selected to serve as dispersant for the extrusion melt step in order to attain the desired average particle size of the resin in the dispersion, which in one embodiment is between about 0.2 and 25 microns and between about 0.5 and 10 microns in another embodiment. In another embodiment, the polyolefin particles may range in size from 0.5 to 1.5 microns.

One of ordinary skill in the art will recognize that the dispersant used to create a relatively stable aqueous dispersion of polyolefin resin particles may vary depending on the nature of the polyolefin particles employed. Additionally, the dispersant used may be the same or different than the froth stabilizing surfactant used in the subsequent preparation of the froth.

Dispersion Formulations

Dispersion formulations in accordance with embodiments disclosed herein may include a liquid medium, such as water, a thermoplastic resin, a dispersion stabilizing agent, and optionally a filler. With respect to the thermoplastic resin and the dispersion stabilizing agent, in some embodiments, the thermoplastic resin may comprise between about 30% to 99% (by weight) of the total amount of base polymer and dispersion stabilizing agent in the composition. In other embodiments, the thermoplastic resin may comprise between about 50% and about 80% (by weight) of the total amount of base polymer and dispersion stabilizing agent in the composition. In yet other embodiments, the thermoplastic resins may comprise about 70% (by weight) of the total amount of base polymer and dispersion stabilizing agent in the composition.

In one embodiment, the aqueous dispersion disclosed herein may include polyolefin resin particles ranging in size from about 0.2 to 10 microns; from about 0.5 to 5 microns in another embodiment; and from about 1 to 2 microns. Thus, in comparison to the thermoplastic fibers mixed with the aqueous dispersion, the polyolefin resin particles are several orders of magnitude smaller than the fibers, discussed further below.

In a particular embodiment, the polyolefin resin may include copolymers and interpolymers of ethylene and/or propylene and other monomers selected from $C_4$ to $C_{10}$ olefins, preferably alpha-olefins, more preferably selected from $C_4$ to $C_8$ alpha-olefins and most preferably selected from n-butene, n-hexene and n-octene. The ethylene or propylene content of the resin may range from about 2 to 98 weight percent of the polyolefin. Where a softer, more flexible foam may be desired, a primarily ethylene-based polyolefin may be selected in which ethylene comprises from about 98 to 50 weight percent of the polyolefin, although propylene based elastomers may also be employed. Where a stiffer foam of greater flexural modulus may be desired, a primarily propylene-based or other polyolefin may be selected in which propylene comprises from about 98 to 50 percent of the polyolefin. Selected comonomer(s) may comprise the remainder of the polyolefin particles.

In one embodiment, the polyolefin resin may include an ethylene-based polyolefin which has a melt index ("MI") determined according to ASTM D1238 (190° C. with a 2.16 kg weight) from about 0.1 to 25 g/10 min; from 0.25 to 22 g/10 min in another embodiment; and from about 0.5 to 18 g/10 min in yet another embodiment. In another embodiment, the polyolefin resin may include a propylene-based polyolefin which has a Melt Flow Rate ("MFR") determined according to ASTM D1238 (230° C. with 2.16 kg weight) of from about 0.25 to 85 g/10 min; from about 0.7 to 70 g/10 min in another embodiment; from about 1.4 to 60 in yet another embodiment; and from about 2 to 50 g/10 min in yet another embodiment.

In one embodiment, the polyolefin resin may comprise an ethylene-based polyolefin having a density ranging from about 0.845 to 0.925 g/cc; from about 0.85 to 0.91 in another embodiment; from about 0.855 to 0.905 in yet another embodiment; and from about 0.86 to 0.90 in yet another embodiment.

One class of polyolefins particularly suited for use in embodiments of the disclosure are copolymers of ethylene and 1-octene or 1-butene, where ethylene comprises from about 50 to 90 percent by weight of the copolymer in one embodiment, and from about 55 to 85 percent by weight of the copolymer in another embodiment, and 1-octene or 1-butene comprises from about 10 to 50 percent by weight of the copolymer in one embodiment and from about 15 to 45 percent by weight of the copolymer in another embodiment, and where the ethylene copolymer has a Melt Index ranging from about 0.25 to 30 g/10 min in one embodiment, and 0.5 to 20 g/10 min in another embodiment.

Another preferred class of polyolefins for use in the disclosure are copolymers of 1-propene and ethylene, 1-octene, 1-hexene or 1-butene, where 1-propene comprises from about 65 to 95 percent by weight of the copolymer in one embodiment, and from about 75 to 93 percent by weight of the copolymer in another embodiment, and ethylene, 1-octene, 1-hexene or 1-butene comprise from about 5 to 35 percent by weight of the copolymer in one embodiment, and from about 7 to 25 percent by weight of the copolymer in another embodiment, and wherein the copolymer has a Melt Flow Rate ranging from about 0.7 to 85 g/10 min in one embodiment and from about 1.4 to 55 g/10 min in another embodiment.

The thermoplastic resin and the dispersion stabilizing agent, are preferably dispersed in a liquid medium, which in some embodiments is water. In some embodiments, sufficient base is added to neutralize the resultant dispersion to achieve a pH range of about 6 to about 14. In particular embodiments, sufficient base is added to maintain a pH between about 9 to about 12. Water content of the dispersion may be controlled so that the combined content of the thermoplastic resin and the dispersion stabilizing agent (solids content) is between about 1% to about 74% (by volume). In another embodiment, the solids content ranges between about 25% to about 74% (by volume). In yet another embodiment, the solid content ranges between about 30% to about 50% (without filler, by weight). In yet another embodiment, the solids content ranges is between about 40% to about 55% (without filler, by weight).

Dispersions formed in accordance with embodiments of the present disclosure may be characterized in having an average particle size of between about 0.3 to about 3.0 microns. In other embodiments, dispersions have an average particle size of from about 0.8 to about 1.2 microns. By "average particle size", the present disclosure means the volume-mean particle size. In order to measure the particle size, laser-diffraction techniques may be employed for example. A particle size in this description refers to the diameter of the polymer in the dispersion. For polymer particles that are not spherical, the diameter of the particle is the average of the long and short axes of the particle. Particle sizes can be measured on a Beckman-Coulter LS230 laser-diffraction particle size analyzer or other suitable device.

In a specific embodiment, a thermoplastic resin, a stabilizing agent, and a filler are melt-kneaded in an extruder along with water and a neutralizing agent, such as ammonia, potassium hydroxide, or a combination of the two to form a dispersion compound. Those having ordinary skill in the art will recognize that a number of other neutralizing agents may be used. In some embodiments, the filler may be added after blending the thermoplastic resin and stabilizing agent.

Any melt-kneading means known in the art may be used. In some embodiments, a kneader, a BANBURY® mixer, single-screw extruder, or a multi-screw extruder is used. A process for producing the dispersions in accordance with the present disclosure is not particularly limited. One preferred process, for example, is a process comprising melt-kneading the above-mentioned components according to U.S. Pat. No. 5,756,659 and U.S. Patent Publication No. 20010011118.

Figure 3:
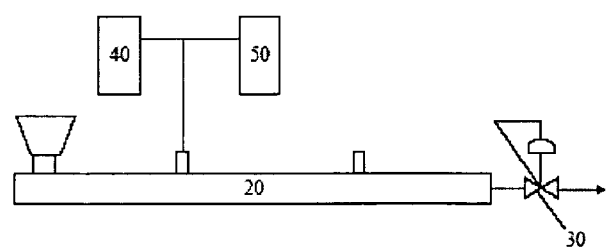
FIG. 3 shows an extruder that may be used to form dispersions in accordance with embodiments disclosed herein.

FIG. 3 schematically illustrates an extrusion apparatus that may be used in embodiments of the disclosure. An extruder 20, in certain embodiments a twin screw extruder, is coupled to a back pressure regulator, melt pump, or gear pump 30. Embodiments also provide a base reservoir 40 and an initial water reservoir 50, each of which includes a pump (not shown). Desired amounts of base and initial water are provided from the base reservoir 40 and the initial water reservoir 50, respectively. Any suitable pump may be used, but in some embodiments a pump that provides a flow of about 150 cc/min at a pressure of 240 bar is used to provide the base and the initial water to the extruder 20. In other embodiments, a liquid injection pump provides a flow of 300 cc/min at 200 bar or 600 cc/min at 133 bar. In some embodiments, the base and initial water are preheated in a preheater.

Those having ordinary skill in the art will recognize that the above list is a non-comprehensive listing of suitable polymers. It will be appreciated that the scope of the present disclosure is restricted by the claims only.

Surfactants

Embodiments of the present disclosure may use a surfactant to promote the formation of a stable dispersion and to aid in frothing. Creating and stabilizing the froth during the frothing and drying steps may be accomplished by addition of a froth stabilizing surfactant to the aqueous dispersion of the polyolefin resin when initially creating the froth. In addition, these surfactants may also be used to improve aqueous wetting of dried foams, if desired.

Suitable froth stabilizing surfactants may be selected from cationic, non-ionic, and anionic surfactants. In one embodiment, an anionic surfactant may be used. Examples of cationic surfactants include quaternary amines, primary amine salts, diamine salts, and ethoxylated amines. Examples of non-ionic surfactants include block copolymers containing ethylene oxide, silicone surfactants, alkylphenol ethoxylates, and linear and secondary alcohol ethoxylates of alkyl group containing more than 8 carbon atoms.

Examples of anionic surfactants include sulfonates, carboxylates, and phosphates. In one embodiment, anionic surfactants useful in preparing the froth from the aqueous dispersion may be selected from carboxylic acid salts and ester amides of carboxylic fatty acids, preferably fatty acids comprising from 12-36 carbon atoms, e.g., stearic or lauric acid, palmitic, myristic, oleic, linoleic, ricinoleic, erucic acid and the like.

In some embodiments, the surfactant may include amphoteric surfactants such as aminopropionates, amphoteric sulfonates, betaines, imidazoline based amphoterics, and sultaines, among others. For example, the surfactant may be derived from an imidazoline and can either be the acetate form (containing salt) or the propionate form (salt-free). Examples of suitable amphoteric surfactants include surfactants such as lauramidopropyl betaine, sodium laurimino dipropionate, cocoamidopropyl hydroxyl sultaine, alkylether hydroxypropyl sultaine, sodium capryloampho hydroxypropyl sulfonate, disodium capryloampho dipropionate, sodium cocoamphoacetate, disodium cocoamphodiacetate, sodium cocoamphopropionate, disodium octyl iminodipropionate, sodium cocoampho hydroxypropyl sulfonate, disodium lauryl iminodipropionate, sodium stearoampho acetate, and disodium tallow iminodipropionate, among others. Other amphoteric surfactants known in the art may also be used.

Surfactants useful as a stabilizing agent may be either external surfactants or internal surfactants. External surfactants are surfactants that do not become chemically reacted into the polymer during dispersion preparation. Examples of external surfactants useful herein include salts of dodecyl benzene sulfonic acid and lauryl sulfonic acid salt. Internal surfactants are surfactants that do become chemically reacted into the polymer during dispersion preparation. An example of an internal surfactant useful herein includes 2,2-dimethylol propionic acid and its salts.

In one embodiment, when a good "hand" or fabric-like feel is desired in the finished foam, a saturated fatty acid derivative (e.g., the salt of stearic or palmitic acid) may be used. Other suitable anionic surfactants include alkylbenzene sulfonates, secondary n-alkane sulfonates, alpha-olefin sulfonates, dialkyl diphenylene oxide sulfonates, sulfosuccinate esters, isothionates, linear alkyl (alcohol) sulfates and linear alcohol ether sulfates. It is understood that the froth stabilizing surfactants may or may not be different than those used to prepare the dispersion. These surfactants serve both to assist in froth formation and help to stabilize the froth. In a particular embodiment, the surfactant may be selected from at least one of alkali metal, mono-, di- and tri-alkanol amine (mono-, di- or triethanol amine, for example), and ammonium salts of lauryl sulfate, dodecylbenzene sulfates, alcohol ethoxy sulfates, and isothionates, the dibasic salt of N-octyldecylsulfosuccinimate, and mixtures thereof. In other embodiments, the froth stabilizing agent may include cellulose.

Fibers

In one embodiment, the fibers may include meltblown fibers formed from thermoplastic polymers including, for example, polyolefins, polyamides, polyester, polyurethane, polyvinyl alcohol, polycaprolactone, styrene butadiene block copolymers or the like. Suitable polyolefins include, for example, polyethylene, polypropylene, polybutylene, copolymers of ethylene with other alpha-olefins, copolymers of propylene with other alpha-olefins, copolymers of butylene with other alpha-olefins, and combinations thereof. In some embodiments, the fibers may include homofil fibers. Alternatively, the thermoplastic fibers may include melt spun or melt drawn fibers formed from any of the thermoplastic polymers listed above. In a particular embodiment, the thermoplastic fibers may comprise a synthetic polyolefin fiber. An example of a commercially available synthetic fiber is FYBREL® E-type Polyethylene synthetic pulp available from MiniFIBERS, Inc. (Johnson City, Tenn.). These fibers may comprise more than 95% polyethylene and less than 5% polyvinyl alcohol and have a melting point of 135° C. and specific gravity of 0.96 g/cm$^3$. In other embodiments, natural fibers may also be used, including cellulosic-based fibers such as cotton or pulp fibers. In yet other embodiments, the fibers are comminuted monofilament type fibers (i.e., fibers divided into smaller parts or fibers having a shortened length).

In one embodiment, the fibers may also incorporate wetting agents within their structure. Wetting agents may comprise additives such as alkoxylated alkyl phenol along with (or in combination with) at least one selected from mono-, di-, and tri-glycerides, and polyoxyalkylene fatty acid esters and combinations thereof. Inclusion of such wetting agents are described in U.S. Pat. No. 4,486,552, which is herein incorporated by reference.

In various embodiments, the foam may comprise from about 10 weight percent to about 60 weight percent fiber based on the combined weight of the thermoplastic resin and fibers; and in other embodiments, from about 10 weight percent to about 40 weight percent fiber based on the combined weight of the thermoplastic resin and fibers. In one embodiment, the fibers may have an average length ranging from 0.2 to 30 mm; from 0.5 to 20 mm in another embodiment; and from 1 to 10 mm in yet another embodiment. In another embodiment, the thermoplastic fibers may have a melting point greater than the melting point of the thermoplastic resin. In some embodiments, the fibers may reduce foam collapse during the froth drying process as compared to drying a similar froth without fibers.

Additives

The foam may optionally contain filler materials in amounts, depending on the application for which they are designed, ranging from about 2-100 percent (dry basis) of the weight of the thermoplastic resin. These optional ingredients may include, for example, calcium carbonate, titanium dioxide powder, polymer particles, hollow glass spheres, polymeric fibers such as polyolefin based staple monofilaments and the like. Foams designed for use in the absorbent articles may contain bulk liquid-absorbing material, such as short cotton fiber or other cellulose fiber evenly distributed throughout the polymer foam.

Although they are not typically blended with the particle dispersion before frothing, due to their strong water absorbent nature, fine particles of super absorbent polymer ("SAP"), such as a lightly cross-linked acrylate polymer, may be evenly distributed upon the surface of the froth just as it is entering the drying process to provide a durable foam with extra absorbent properties on that surface when dried. However, if SAP particles are treated (e.g., with a surface layer of delayed water-solubility polymer such as, for example, a hydroxypropyl alkylcellulose ether or a polyoxyethylene resin), to reduce the particles' initial rate of water absorbency until after the froth has reached the dry foam state, such "retarded-absorbency" SAP particles may beneficially be added directly to the particle dispersion before frothing is initiated.

The superabsorbent polymer ("SAP") particles useful in embodiments disclosed herein are those that absorb many times their own weight of the fluid in question, such as moisture, water or aqueous liquids. SAP particles swell when they absorb the fluid. SAPs are used in a variety of applications, including diapers, water-barrier applications in the construction industry, and liquid absorbers in food-packaging systems, as well as in hygiene and medical applications. SAP particles can be any of the known hydrophilic polymers that are cross-linked and capable of absorbing large quantities of aqueous fluids, in some instances causing the particle to swell up to several times its dry size. These polymers are well known in the art and are widely available commercially. Most SAPs are crosslinked, partially neutralized and/or surface treated. Preferably, the level of crosslinking is selected to give the desired swelling characteristics for the particular application.

Examples of some suitable SAPs and processes (including gel polymerization processes) for preparing SAPs are disclosed in U.S. Pat. Nos. 3,669,103; 3,670,731; 3,926,891; 3,935,099; 3,997,484; 4,076,663; 4,090,013; 4,093,776; 4,190,562; 4,286,082; 4,340,706; 4,446,261; 4,459,396; 4,654,039; 4,683,274; 4,708,997; 4,857,610; 4,985,518; and 5,145,906, the teachings of which are incorporated herein by reference. In addition, see Buchholz, F. L. and Graham, A. T., "Modern Superabsorbent Polymer Technology," John Wiley & Sons (1998) and Lisa Brannon-Peppas and Ronald S. Harland, "Absorbent Polymer Technology" Elsevier (1990).

Froth Preparation

A froth may be prepared from the dispersion/surfactant/fiber mixture by using a mechanical method such as a high shear, mechanical mixing process under atmospheric conditions to entrain air or other gases in the aqueous phase of the dispersion or optionally injecting gas into the system while mixing. The amount of air or other gas (where a gas in addition to or other than air is desirable) that may be incorporated in the froth may comprise at least 80% by volume in one embodiment, at least 85% by volume in another embodiment, and at least 90% by volume of the resultant froth in yet another embodiment. Initially, all components to be used in making the froth may be mixed together with mild agitation to avoid entrapping air.

Once all of the ingredients are well mixed, the mixture may be exposed to high shear mechanical mixing. During this step, the bulk viscosity of the mixture may increase as more air is entrapped within the continuous aqueous phase until a non-flowable, stiff froth is formed. The mixing time necessary to obtain a froth with the desired density may vary with amount and type of froth stabilizing surfactant and the amount of mechanical shear. Any mechanical mixing device capable of whipping air into a thickened aqueous dispersion, such as a kitchen blender/hand mixer, Hobart mixer fitted with a wire whip, or, on a larger scale, a Cowie-Riding Twin Foamer (Cowie Riding Ltd.) may be used. The commercial foamers may also allow one to inject air into their high shear mixing head to obtain very low (less than 50 g/L) density froth.

Froth density may be measured, for example, by drawing off samples of the froth in cups of predetermined volume and weight, weighing the froth-filled cup and then calculating the density of the sample. In commercial frothers, air can be added directly into the mixing head to assist in development of low density froth. The speed of the frothing device may be increased or decreased to attain a desired froth density. In one embodiment, the froth density may be in a range of about 0.04-0.15 g/cc, and between 0.07-0.08 g/cc in another embodiment. Once a desired density of the froth is obtained, the froth may be optionally spread on a substrate prior to conversion of the froth into a foam.

Frothed foams comprising the polymers may also be formed as disclosed in PCT application No. PCT/US2004/027593, filed Aug. 25, 2004, and published as WO2005/021622. In other embodiments, the polymers may also be crosslinked by any known means, such as the use of peroxide, electron beam, silane, azide, gamma irradiation, ultraviolet radiation, or other cross-linking techniques. The polymers may also be chemically modified, such as by grafting (for example by use of maleic anhydride (MAH), silanes, or other grafting agent), halogenation, amination, sulfonation, or other chemical modification.

Drying and Recovery Steps

In one embodiment, the foam may be prepared from the froth by removing at least a portion of the liquid/aqueous element of the froth prepared as disclosed herein. In other embodiments, the foam may be prepared from the froth by removing at least a majority of the liquid/aqueous element of the froth. In yet other embodiments, the foam may be prepared by removing substantially all of the liquid/aqueous element. In various embodiments, greater than 30 weight percent, greater than 50 weight percent, greater than 80 weight percent, greater than 90 weight percent, greater than 95 weight percent, greater than 98 weight percent, or greater than 99 weight percent of the liquid/aqueous element may be removed. The means by which the liquid portion is removed may be selected to minimize the amount of froth volume collapse. In one embodiment, the froths may be dried and converted to foams by heating in a forced air drying oven, at temperatures selected for optimum drying. In one embodiment, the froth may be heated to a temperature between about 60° and 120° C.

As the nature of the thermoplastic resin permits, processing may be conducted at the highest temperature feasible to remove water as rapidly as possible from the froth without destroying the viscosity of the polyolefin resin particles on the surface of the bubbles of the froth or causing significant (e.g., more than 30 volume percent) collapse of the partially dried froth. In another embodiment, the drying temperature may be selected so as to not exceed the melting point temperature of the thermoplastic fibers. In one embodiment, it may be desirable to dry the froth at a temperature that approaches, but does not exceed the melting range of the thermoplastic resin. In another embodiment, it may be desirable to attain a temperature where the amorphous regions in the thermoplastic resin begin to coalesce while pseudo-crosslinking with the fibers and avoid or at least minimize collapse of the froth before the foam has become fully "dried" in its ultimate form and dimension and at least 95 weight percent of the water in the froth has been driven out. The resulting "dried" foam may have a density of about 0.02 to 0.07 g/cm$^3$ in one embodiment, and from about 0.03 to 0.05 g/cm$^3$ in another embodiment.

Some embodiments of the dried foam may have an average thickness ranging from 0.01 cm to 2.5 cm. Other embodiments of the dried foam may have an average thickness ranging from 0.05 cm to 2.0 cm; and from 1 to 1.5 cm in yet other embodiments. Articles comprising embodiments of the dried foam may include at least one layer of foam having an average thickness ranging from 0.1 cm to 2.5 cm; from 0.5 cm to 2.0 cm in other embodiments; and from 1.0 cm to 1.5 cm in yet other embodiments. In some embodiments, two or more foams may be laminated together; in various embodiments, the two or more foams may have the same or different densities, the same or different cell sizes, or the same or different structures (fibrillated, open-celled, closed celled, etc.). In other embodiments, one or more foams may be laminated to a substrate, such as film.

Drying of the froth to form the desired foam of the disclosure may be conducted in batch or continuous mode. Devices including, for example, conventional forced air drying ovens or banks of infrared heating lamps or dielectric heating devices, e.g., radio (typically operated at permitted frequency bands in the range between 1-100 MHz) and microwave (typically operated at permitted frequency bands in the range between 400 to 2500 MHz) frequency energy generating sources, lining a tunnel or chamber in which the froth may be placed or conveyed through, in a continuous fashion, may be employed for drying. A combination of such drying energy sources may be used, either simultaneously or sequentially applied, to dry a froth to form a foam. In one embodiment, the drying includes the simultaneous use of a dielectric device and a forced air drying oven. For foam having a thickness of about 0.25-0.6 cm, the drying may be achieved as quickly as 45-90 seconds when the forced air oven is operated at approximately 75° C. and a radio frequency generator heats the froth to an internal temperature of about 45-50° C. The temperature of the drying operation may be selected according to the nature and the melting range of the polyolefin resin (as determined by DSC) employed to prepare the foam. The dielectric heating frequency bands, permitted for industrial use in various countries, are designated in greater detail in the reference "Foundations of Industrial Applications of Microware and Radio Frequency Fields", Rousy, G and Pierce, J. A. (1995).

Foam Structure

Figure 5:
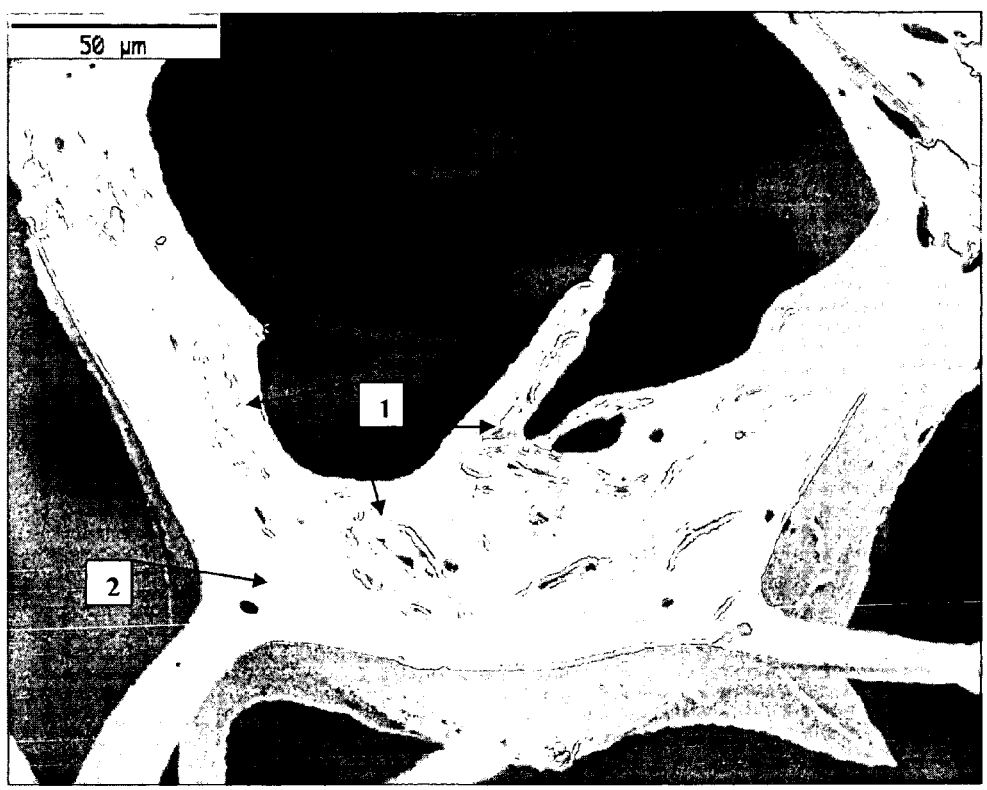
FIG. 5 shows an SEM image, at 50 μm resolution, of a polyolefin foam made in accordance with one embodiment disclosed herein.
Figure 6:
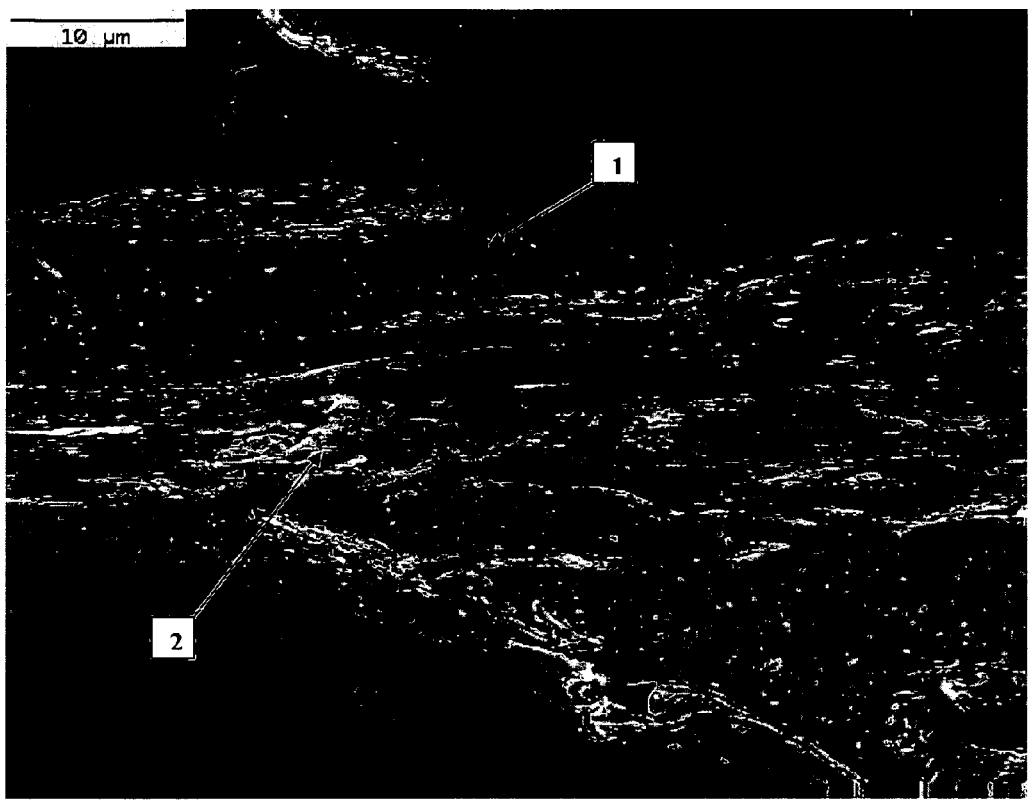
FIG. 6 shows a close up SEM image, at 10 μm resolution, of a cross-section of a strut of the polyolefin foam made in accordance with one embodiment disclosed herein.

When embodiments of the fibers and dispersions are combined, frothed, and dried to form a foam, each as described above, a fibrillated structure may result. As described further in Example 3 below with reference to FIGS. 4-6, the strut-like structure of the foam includes thermoplastic fibers 1 and thermoplastic resin 2, where the thermoplastic resin 2 surrounds and interconnects the fibrous network, forming a continuous web. The fibrillated structure may be cellular or, as shown in FIGS. 4-6, non-cellular in appearance. The foam morphology may also be characterized as having a high degree of randomness and larger surface openings as compared to traditional PFFs. The internal structure of the foam may also display a non-cellular architecture with non-woven fibrils and larger void spaces relative to conventional PFFs.

In one embodiment, the absorbent structure (the foam) may have a non-cellular, fibrillated morphology. As used herein, a "non-cellular, fibrillated structure" refers to a foam having an open, random, non-cellular, morphology composed of or having fibrils or thread-like filaments. The non-cellular, fibrillated structure, for example, may be non-uniform and nonrepeating, such as where the fibrils form a non-woven fibrous-like web and where a majority of the struts are not interconnected.

In another embodiment, the foam may have an insult strike through rate ranging from about 0.1 to about 10 seconds, based upon a 5.0 mL liquid insult of synthetic urine at 23° C. on a foam sample size of 50 cm$^2$. In yet another embodiment, the foam may have an insult strike through rate ranging from about 0.5 to 7 seconds; and from about 1 to 4 seconds in yet other embodiments. In yet another embodiment, the foam may have an average thickness ranging from about 0.03 to 3.0 cm; from about 0.1 to about 2.5 cm in other embodiments; from about 0.5 to about 2.0 cm in other embodiments; and from about 1.0 to about 1.5 cm in yet other embodiments.

Hygiene Articles

In one embodiment of the disclosure, the foams disclosed herein may be used in fabrication of the absorbent core structure of hygiene articles; e.g., diapers, incontinent briefs, training pants, diaper holders and liners, feminine hygiene garments, and the like, designed to provide improved fit and comfort for the wearer while adequately containing body exudates.

The absorbent core refers to the portions (e.g., layers) of an absorbent article whose functions are to acquire, distribute, transfer, store and/or redistribute fluid. The absorbent core comprises absorbent material, at least one of which comprises the foam of the disclosure, and is capable of acquiring, distributing and/or retaining liquids such as urine and certain other body exudates, in suitable manner and degree.

In other embodiments, it may be desirable to form an article having two or more foam layers. In some embodiments, the foam layers may be of the same or different density. In other embodiments the two or more foam layers may be laminated.

EXAMPLES

The following examples include exemplary froth foams and experimental data showing their effectiveness in absorbency applications. Foams may be characterized by various methods including SEM imaging, 45 degree run-off measurements, percent collapse when subjected to a load, strikethrough times (Edana 150.4-99), and absorption capacity index.

Foams were generated from dispersions formed with polyolefin elastomers (ENGAGE®) or polyolefin plastomers (AFFINITY™) (each available from The Dow Chemical Company, Midland, Mich.) and polyethylene pulp (Polyethylene Fiber Type E available from MiniFIBERS, Inc., Johnson City, Tenn.) in accordance with the protocols detailed herein. The following procedure is exemplary and variants may be carried out by adjusting to desired fiber loadings, dilutions, and surfactant usage.

Dispersion: An aqueous dispersion of a polyolefin plastomer is formed in accordance with the procedures as described in WO2005021638. The dispersion is formed using AFFINITY™ EG 8200 (an ethylene-alpha olefin copolymer having an MI2 of about 5 dg/min, and a density of 0.870 g/cc). The dispersion surfactant system includes UNICID® (a linear carboxylic acid available from Baker Petrolite), HYSTRENE® (a fatty acid available from Crompton Corp., Greenwich, Conn.), and METHOCEL® (a water-soluble methylcellulose and hydroxypropyl methylcellulose polymer available from The Dow Chemical Company), used at a loading of 2 weight percent, 1 weight percent, and 0.2 weight percent, respectively, based on the combined weight of the ethylene copolymer and the surfactant system. The aqueous dispersion produced has a solids content of approximately 53 weight percent.

Foam: To produce a foam with 40% fiber loading, 10 gallons of the above described dispersion (POD 8102, The Dow Chemical Company, Midland, Mich.) are mixed with 1.5 weight percent ammonium laureth sulfate (STEOL®, available from Stepan Co., Northfield, Ill.) and 1 weight percent sodium lauryl sulfate (STEPANOL®, also available from Stepan Co.), based on polymer solids (a 2-1-1 dispersion, having 2 parts stabilizing agent, 1 part froth stabilizing surfactant, and 1 part wetting agent). An 80 gram aliquot of the dispersion is placed in a mixing bowl and diluted further with 80 grams of de-ionized water. The mixture is stirred at a low setting for one minute, and then 15 grams of synthetic fibers (Polyethylene Fiber Type E, available from MiniFIBERS, Inc., Johnson City, Tenn.) are added with continued slow stirring over two minutes. The froth is created by stirring at high speed (Hobart mixer equipped with a whisk) for one to two minutes. The froth is laid on release paper and smoothed to a height ranging from about 0.1 cm to about 2.54 cm with the aid of a screeding tool. The froth is then dried in a preheated oven at 75° C. to form the foam.

Example 1

Three foam samples are prepared according to the above procedure. Sample 1 foam contains no fibers and uses the above described 2-1-1 dispersion of AFFINITY™ EG 8200 (POD 8102, The Dow Chemical Company, Midland, Mich.) and 1.5% STEOL® based on polymer solids. Samples 2 and 3 use a 40% fiber loading with polyethylene fibers (Polyethylene Fiber Type E available from MiniFIBERS, Inc., Johnson City, Tenn.), in addition to the 1.5% STEOL®, both based on polymer solids. Sample 2 is made with 2-1-1 POD 8102 dispersion whereas Sample 3 uses a 2-1-2 POD 8102 dispersion.

Strike through experiments, testing the speed at which a liquid passes through the foam structure, and Absorbent Capacity Index (ACI) measurements are carried out on these foam samples prepared in accordance with the details disclosed above.

The liquid used for the strike through measurements is a 5.0 mL sample of synthetic urine (as described in U.S. Pat. No. 5,260,345) at 23° C. with a foam sample size of 50 cm$^2$. Liquid is introduced to the top and bottom of the samples. The results of the strike through test, with each entry being an average of 4 runs, are shown in Table 1 below.

TABLE 1

Strike Through Summary

| Sample | Fibers (%) | Thick (cm) | Wt (g) | Basis Wt (g/m$^2$) | Density (g/cc) | Strike Through Time (sec) |
|---|---|---|---|---|---|---|
| 1 Top | 0 | 0.217 | 0.458 | 92 | 0.042 | 3.86 |
| 1 Bottom | 0 | 0.217 | 0.450 | 90 | 0.042 | 3.63 |
| 2 Top | 40 | 0.193 | 0.416 | 83 | 0.043 | 1.81 |
| 2 Bottom | 40 | 0.192 | 0.425 | 85 | 0.044 | 1.48 |
| 3 Top | 40 | 0.235 | 0.490 | 98 | 0.042 | 1.53 |
| 3 Bottom | 40 | 0.244 | 0.493 | 99 | 0.040 | 1.42 |

As shown in Table 1, there is a dramatic decrease in strike through for samples containing the polyolefin fibers. Whether the wetting load was introduced to the top or bottom of the foam sample did not appear to effect strike through.

ACI measurements use the same synthetic urine described above with a foam sample sizes of 50 cm$^2$, introducing 24.9 mL of synthetic urine at a rate of 7.0 mL/second. Table 2, below, summarizes the absorption data for these foam samples, with each entry being an average of 6 runs.

TABLE 2

Absorption Summary

| Sample | Avg. Thickness (cm) | Wt (g) | Basis Wt (g/m$^2$) | Density (g/cc) | ACI (No Load) (g/g) |
|---|---|---|---|---|---|
| 1 | 0.288 | 0.472 | 94 | 0.033 | 25 |
| 2 | 0.270 | 0.447 | 89 | 0.033 | 32 |
| 3 | 0.271 | 0.488 | 98 | 0.036 | 28 |

As shown in Table 2, ACI increases for the samples containing 40% polyethylene fibers (Samples 2 and 3) relative to the foam sample containing no fibers (Sample 1).

Example 2

Foam samples are synthesized in accordance with the protocol outlined above. Polyolefin dispersions (POD 8102) are variably diluted and incorporate varied fiber loadings with polyethylene pulp (Polyethylene Fiber Type E available from MiniFIBERS, Inc., Johnson City, Tenn.). Fiber loadings shown in Table 3 are based upon the weight of polymer solids. Sample foams are 15.3 cm×10.2 cm. These samples are subjected to 45 Degree Run-off test carried out by placing the foam sample on a surface at a 45 degree angle and introducing two 80 mL liquid insults to the top of the foam, and collecting and measuring the quantity of any liquid run-off not absorbed by the foam. The liquid insults are introduced five minutes apart, and the run-off measurements are reported as 1$^{st}$ and 2$^{nd}$ Run-off, respectively. The foam collapse represents the amount of froth collapse during curing. The liquid insult is synthetic urine formulated as 0.03 weight percent calcium chloride, 0.08 weight percent magnesium sulfate, 0.77 weight percent sodium chloride, 1.94 weight percent urea, and 97.17 weight percent de-ionized water. The results of these tests are summarized in Table 3 below.

TABLE 3

Fiber Loading and 45 Degree Run-off Testing

| Sample | Cup wt. (g) | fibers (%) | Dispersion:DI-H$_2$O (g:g) | Surf. (g) | Thickness (cm) | Weight (g) | Density (g/cm$^3$) | Basis wt. (g/m$^2$) | 1st Run-off (g) | 2nd Run-off (g) | Collapse (%) |
|---|---|---|---|---|---|---|---|---|---|---|---|
| 4 | 3.75 | 9.4 | 80:40 | 2.5 | 0.153 | 0.985 | 0.041 | 63 | 7.3 | 0.59 | 65 |
| 5 | 5.06 | 9.4 | 80:20 | 2.5 | 0.213 | 1.485 | 0.045 | 95 | 3.3 | 7.55 | 52 |
| 6 | 10.35 | 9.4 | 80:0 | 2.5 | 0.344 | 3.19 | 0.059 | 204 | 9.2 | 34.20 | 22 |
| 7 | 3.86 | 20 | 80:80 | 2.5 | 0.127 | 0.795 | 0.040 | 51 | 4.5 | 0.00 | 71 |
| 8 | 4.69 | 20 | 80:40 | 2.5 | 0.195 | 1.25 | 0.041 | 80 | 3.5 | 0.00 | 56 |
| 9 | 9.49 | 20 | 80:20 | 2.5 | 0.330 | 2.395 | 0.046 | 153 | 11.7 | 22.01 | 25 |
| 10 | 20.8 | 20 | 120:0 | 2.5 | 0.460 | 8.445 | 0.117 | 541 | 19.4 | 48.31 | −5 |
| 11 | 4.1 | 30 | 80:80 | 2.5 | 0.151 | 0.89 | 0.038 | 57 | 3.8 | 0.00 | 66 |
| 12 | 10.06 | 30 | 80:40 | 2.5 | 0.382 | 2.89 | 0.048 | 185 | 8.4 | 9.18 | 13 |
| 13 | 5.1 | 40 | 80:80 | 2.5 | 0.207 | 1.27 | 0.039 | 81 | 1.0 | 0.00 | 53 |
| 14 | 7.67 | 50 | 80:80 | 2.5 | 0.301 | 1.945 | 0.042 | 125 | 1.3 | 0.00 | 32 |
| 15 | 6.32 | 0 | 80:0 | 0.0 | 0.306 | 1.975 | 0.041 | 127 | 3.9 | 50.57 | 31 |
| 16 | 3.1 | 0 | 80:80 | 2.5 | 0.071 | 0.535 | 0.048 | 34 | 11.1 | 0.45 | 84 |
| 17 | 3.42 | 0 | 80:40 | 2.5 | 0.138 | 0.825 | 0.038 | 53 | 7.5 | 0.96 | 69 |
| 18 | 3.46 | 0 | 80:20 | 2.5 | 0.167 | 0.98 | 0.038 | 63 | 9.5 | 3.57 | 62 |
| 19 | 4.63 | 0 | 80:0 | 2.5 | 0.231 | 1.565 | 0.043 | 100 | 5.3 | 2.36 | 47 |
| 20 | 4.71 | 0 | 80:80 | 0 | 0.160 | 0.875 | 0.035 | 56 | 11.3 | 40.40 | 64 |
| 21 | 4.64 | 0 | 80:40 | 0 | 0.219 | 1.075 | 0.031 | 69 | 9.8 | 32.90 | 50 |
| 22 | 5.16 | 0 | 80:20 | 0 | 0.251 | 1.345 | 0.034 | 86 | 9.0 | 48.59 | 43 |

Comparing samples having constant fiber loading, an increase in the dilution of the polyolefin dispersion generally led to increased collapse (cf. samples 4-6 or 7-10). As fiber loads are increased, there is a dramatic reduction in collapse due to the presence of the fibers as compared to foams created without fibers (cf. samples 6, 10, 15 and 19), suggesting that the fibers may help support the integrity of the struts within the foam structure. The run-off testing indicated that in the foams created without fibers, run-off amounts were generally higher. Thus a balance must be found in dilution levels to minimize run-off without leading to increased collapse. The addition of fibers in the foams disclosed herein may play an integral role in striking this balance to effectively reduce foam collapse.

Example 3

Figure 1A:
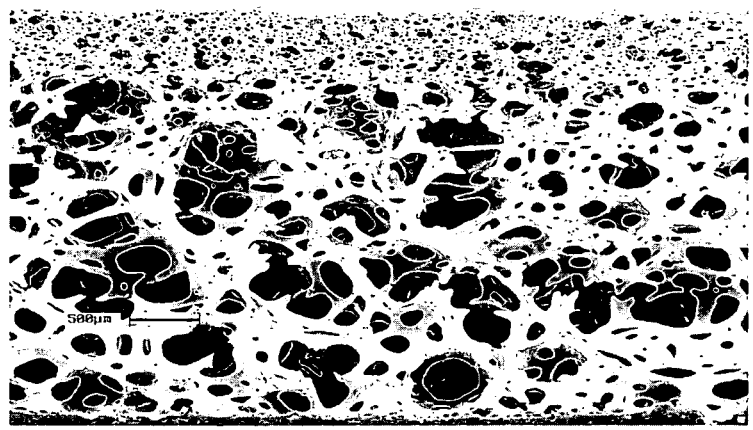
FIGS. 1a-1b show SEM images of a cross section (1a) and surface (1b) of a polyolefin foam made by the conventional method.
Figure 1B:
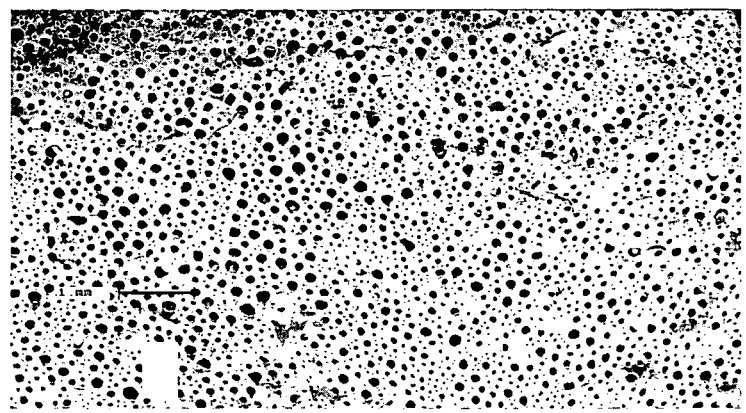
Figure 4A:
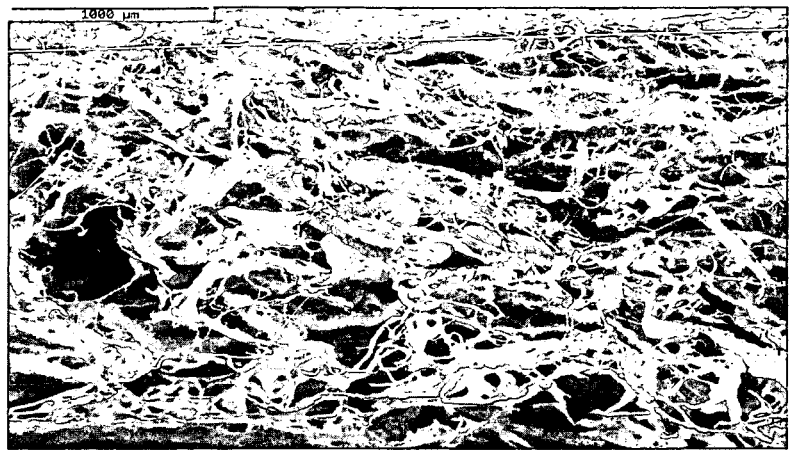
FIGS. 4a-4b show SEM images, at 1000 μm resolution, of a cross section (3a) and surface (3b) of a polyolefin foam made in accordance with one embodiment disclosed herein.
Figure 4B:
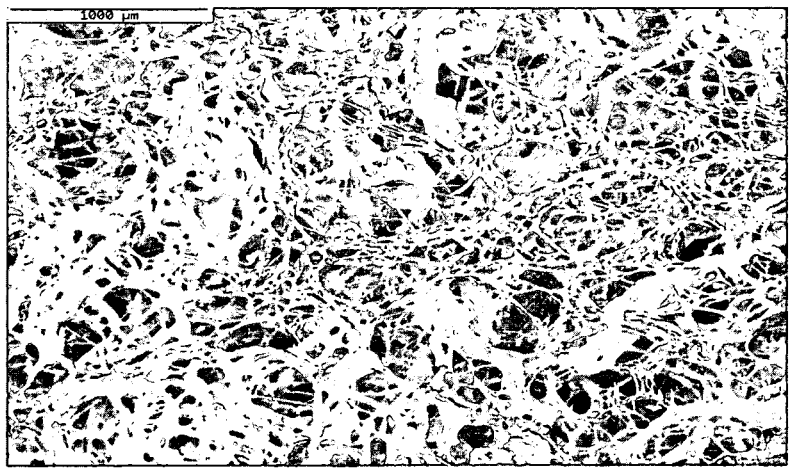

SEM images of samples of polyolefin foams made in accordance with the above outlined protocol are illustrated in FIGS. 4a and 4b. The foam formed from an aqueous dispersion of AFFINITY™ with incorporated polyolefin fibers displays a novel, non-cellular, fibrillated structure. The morphology of the foams may be characterized as having a high degree of randomness and larger surface openings as compared to the traditional PFFs shown in FIGS. 1a-b. The cross-section of the foam shown in FIG. 4a also displays a non-cellular architecture with non-woven fibrils and large void spaces. The larger surface openings, as shown in FIG. 4b, may allow for faster liquid strike through and the larger void spaces may result in lower capillary pressure for liquid retention.

High resolution SEM images of the foam struts show that the polyethylene fibers are substantially encapsulated by the AFFINITY™ polymer, as shown in FIGS. 5 and 6. In FIG. 5, a high resolution image of a strut in the foam structure shows the polyolefin fibers 1, within the matrix of the AFFINITY™ polymer 2, which makes up the bulk of the strut structure. Fibers 1 provide reinforcement of the strut structure. FIG. 6 is a high resolution SEM image of a cross section of a strut, and shows the AFFINITY™ polymer 1 surrounding the polyethylene fibers 2.

While references to the use of the disclosed foams in absorbent materials for personal hygiene articles may have been made, no limitation on the present disclosure was intended by such description. Rather the foams disclosed herein may specifically find use in household and personal care wipes, medical wound care and surgical dressings, air and liquid filtrations, food absorption pads such as chicken or meat pads, fabric/textile backing, noise/sound deadening, and auto IP backing.

Advantages of embodiments of the disclosure may include one or more of the following. The reticulated morphology may allow for larger foam surface openings that may result in faster liquid absorption and faster liquid strike through. The larger void spaces may result in lower capillary pressure for reduced liquid retention versus traditional froth foam morphology. The foam described in herein may exhibit superior wet and dry tensile strength and superior wet collapse compared to cellulose based fiber systems. Additionally, the elastomeric nature of various foams may also allow the foam to retain shape. Advantageously, in some embodiments, the fibers may act as a collapse stabilizing agent, reducing froth collapse during film formation and/or reducing dry foam collapse.

While the disclosure has been described with respect to a limited number of embodiments, those skilled in the art will appreciate that other embodiments can be devised which do not depart from the scope of the disclosure as disclosed herein. Accordingly, the scope of the disclosure should be limited only by the attached claims.

What is claimed is:

1. A method for generating a thermoplastic non-cellular fibrillated foam, the method comprising:
   melting a thermoplastic resin and dispersion stabilizing agent in a fist part of an extruder to form a polymer melt;
   adding water to the polymer melt to form an aqueous dispersion in a second part of the extruder;
   adjusting the pH of the aqueous dispersion to between 8 and 11;
   adding at least one froth stabilizing surfactant to the aqueous dispersion to form a mixture;
   adding fiber to the mixture,
      wherein the fiber comprises at least one of a polyethylene homopolymer, copolymer, or multiblock interpolymer, a polypropylene homopolymer, copolymer, or multiblock interpolymer, and combinations thereof; and
      wherein the fiber has an average length in the range from about 0.2 to about 30 mm; and
      wherein the fiber is present in the range from about 30 wt. % to about 60 wt. % based on a total weight of the thermoplastic resin and the fiber;
   frothing the mixture to create a froth, and
   removing at least a portion of the water in the froth to create a foam,
   wherein the foam generated has a non-cellular fibrillated morphology.

2. The method of claim 1, further comprising:
   coating at least a portion of a substrate with a layer of the froth; and
   removing a majority of the water from the froth.

3. The method of claim 1, wherein the removing at least a portion of the water in the froth to create a foam results in a foam having from 0 to 20 weight percent residual water.

4. The method of claim 1, wherein the dispersion stabilizing agent comprises a fatty acid.

5. The method of claim 1, wherein the froth stabilizing surfactant comprises cellulose.

6. The method of claim 1, wherein the dispersion comprises from about 25 to about 74% thermoplastic resin and dispersion stabilizing agent by volume of the dispersion.

7. The method of claim 1, wherein the dispersion comprises from about 40 to about 55 percent thermoplastic resin and dispersion stabilizing agent by weight, exclusive of any filler.

8. The method of claim 6, wherein the thermoplastic resin comprises a polyolefin.

9. The method of claim 1, wherein the fibers have a melting point greater than the thermoplastic resin.

10. The method of claim 1, wherein the foam has at least one layer having an average thickness of from about 0.01 cm to about 2.5 cm.

11. The method of claim 1, wherein the fiber has an average length in the range from about 0.5 to about 20 mm.

12. A method for generating a thermoplastic non-cellular fibrillated foam, the method comprising:
   melting a thermoplastic resin and a dispersion stabilizing agent in a first part of an extruder to form a polymer melt in a second part of the extruder;
   adding water to the polymer melt to form an aqueous dispersion;
   adjusting the pH of the aqueous dispersion to between 8 and 11;
   adding at least one froth stabilizing surfactant to the aqueous dispersion to form a mixture;
   adding fiber to the mixture,
      wherein the fiber comprises at least one of a polyethylene homopolymer, copolymer, or multiblock interpolymer, a polypropylene homopolymer, copolymer, or multiblock interpolymer, and combinations thereof; and
      wherein the fiber has an average length in the range from about 0.2 to about 30 mm; and
      wherein the fiber is present in the range from about 30 wt. % to about 60 wt. % based on a total weight of the thermoplastic resin and the fiber;
   frothing the mixture to create a froth; and
   removing at least a portion of the water in the froth to create a foam;
   wherein the foam created comprises 20 weight percent or less residual water; and
   wherein the foam generated has a non-cellular fibrillated morphology.

13. The method of claim 12, wherein the dispersion stabilizing agent comprises a fatty acid.

14. The method of claim 12, wherein the froth stabilizing surfactant comprises cellulose.

15. The method of claim 12, further comprising coating at least a portion of a substrate with a layer of froth.

16. The method of claim 12, wherein the dispersion comprises from about 25 to about 74% thermoplastic resin and dispersion stabilizing agent by volume of the dispersion.

17. The method of claim 12, wherein the thermoplastic resin comprises a polyolefin.

18. The method of claim 12, wherein the fibers have a melting point greater than the thermoplastic resin.

19. The method of claim 12, wherein the foam has at least one layer having an average thickness of from about 0.01 cm to about 2.5 cm.

20. The method of claim 12, wherein the resulting foam comprises from 0 to 10 weight percent residual water.

21. The method of claim 12, wherein the resulting foam comprises from 0 to 8 weight percent residual water.

22. The method of claim 12, wherein the dispersion comprises from about 40 to about 55 percent thermoplastic resin and dispersion stabilizing agent by weight, exclusive of any filler.

23. The method of claim 12, wherein the fiber has an average length in the range from about 1 to about 10 mm.

* * * * *